(12) United States Patent
Paul, Jr. et al.

(10) Patent No.: US 8,398,663 B2
(45) Date of Patent: *Mar. 19, 2013

(54) VALVULOTOME DEVICE AND METHOD

(75) Inventors: Ram H. Paul, Jr., Bloomington, IN (US); Brian C. Case, Lake Villa, IL (US); Jacob A. Flagle, New Palastine, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 347 days.

This patent is subject to a terminal disclaimer.

(21) Appl. No.: 12/781,300

(22) Filed: May 17, 2010

(65) Prior Publication Data

US 2010/0286719 A1 Nov. 11, 2010

Related U.S. Application Data

(63) Continuation-in-part of application No. 11/070,130, filed on Feb. 28, 2005, now Pat. No. 7,717,930.

(60) Provisional application No. 60/548,246, filed on Feb. 27, 2004, provisional application No. 60/581,852, filed on Jun. 21, 2004.

(51) Int. Cl.
*A61B 17/22* (2006.01)

(52) U.S. Cl. ....................................... 606/159

(58) Field of Classification Search ............... 606/110, 606/159, 167, 170; 600/36
See application file for complete search history.

(56) References Cited

U.S. PATENT DOCUMENTS

| | | | |
|---|---|---|---|
| 3,837,345 A | 9/1974 | Matar | |
| 4,493,321 A | 1/1985 | Leather | |
| 4,655,217 A | 4/1987 | Reed | |
| 4,768,508 A | 9/1988 | Chin et al. | |
| 4,791,913 A | 12/1988 | Maloney | |
| 4,952,215 A | 8/1990 | Ouriel et al. | |
| 5,049,154 A | 9/1991 | Quadri | |
| 5,069,679 A | 12/1991 | Taheri | |
| 5,087,264 A | 2/1992 | Miller et al. | |
| 5,092,872 A | 3/1992 | Segalowitz | |
| 5,133,725 A | 7/1992 | Quadri | |
| 5,139,506 A | 8/1992 | Bush | |
| 5,141,491 A | 8/1992 | Bowald | |
| 5,171,316 A | 12/1992 | Mehigan | |
| 5,234,450 A | 8/1993 | Segalowitz | |
| 5,284,478 A | 2/1994 | Nobles et al. | |
| 5,304,189 A | 4/1994 | Goldberg | |
| D351,022 S | 9/1994 | Saito | |
| 5,352,232 A | 10/1994 | Cohen | |
| 5,514,151 A | 5/1996 | Fogarty et al. | |
| 5,522,824 A | 6/1996 | Ashby | |
| 5,527,327 A | 6/1996 | Louw et al. | |
| 5,584,842 A | 12/1996 | Fogarty | |
| 5,624,455 A | 4/1997 | Matsuno | |
| 5,626,578 A | 5/1997 | Tihon | |
| 5,658,282 A | 8/1997 | Daw et al. | |
| 5,658,301 A | 8/1997 | Lemaitre et al. | |
| 5,658,302 A | 8/1997 | Wicherski et al. | |

(Continued)

FOREIGN PATENT DOCUMENTS

EP 321132 A2 12/1988
EP 321132 A3 12/1988

(Continued)

*Primary Examiner* — Ryan Severson
(74) *Attorney, Agent, or Firm* — Buchanan Nipper

(57) ABSTRACT

Valvulotome devices and methods are provided. Valvulotome devices include one or more valvulotome arms that have a u-shaped curved body with opposing arms and a base portion that extends between the arms. The valvulotome arm defines a notch open at one end on one of the arms and extending into the base portion of the u-shaped curved body. The notch defines an angled surface that provides a cutting edge. Methods of making valvulotome devices are also described.

20 Claims, 23 Drawing Sheets

| U.S. PATENT DOCUMENTS | | | |
|---|---|---|---|
| 5,707,389 A | 1/1998 | Louw et al. | |
| 5,749,882 A | 5/1998 | Hart et al. | |
| 5,846,241 A | 12/1998 | Kittur et al. | |
| 5,868,768 A | 2/1999 | Wicherski et al. | |
| 5,947,994 A | 9/1999 | Louw et al. | |
| 5,997,557 A | 12/1999 | Barbut et al. | |
| 6,178,968 B1 | 1/2001 | Louw et al. | |
| 6,200,336 B1 | 3/2001 | Pavcnik et al. | |
| 6,267,758 B1 | 7/2001 | Daw et al. | |
| 6,391,050 B1 | 5/2002 | Broome | |
| 6,508,833 B2 | 1/2003 | Pavcnik et al. | |
| 6,565,588 B1 | 5/2003 | Clement et al. | |
| 2003/0125759 A1 | 7/2003 | Mirizzi et al. | |
| 2003/0125795 A1 | 7/2003 | Pavcnik et al. | |
| 2003/0144670 A1 | 7/2003 | Pavcnik et al. | |
| 2004/0167619 A1 | 8/2004 | Case et al. | |
| 2004/0186558 A1 | 9/2004 | Pavcnik et al. | |
| 2004/0204730 A1 | 10/2004 | Goldberg et al. | |
| 2004/0260389 A1 | 12/2004 | Case et al. | |

| FOREIGN PATENT DOCUMENTS | | | |
|---|---|---|---|
| EP | 321132 B1 | 12/1988 | |
| EP | 511323 B1 | 11/1990 | |
| EP | 558039 A2 | 2/1993 | |
| EP | 558039 A3 | 2/1993 | |
| EP | 741544 B1 | 12/1994 | |
| EP | 772421 B1 | 12/1995 | |
| WO | WO8907914 | 9/1989 | |
| WO | WO9101689 | 2/1991 | |
| WO | WO9208414 | 5/1992 | |
| WO | WO9519737 | 7/1995 | |
| WO | WO9528888 | 11/1995 | |
| WO | WO9714362 | 4/1996 | |
| WO | WO9633662 | 10/1996 | |
| WO | WO9639950 | 12/1996 | |
| WO | WO9716125 | 5/1997 | |
| WO | WO9718767 | 5/1997 | |
| WO | WO9824379 | 6/1998 | |
| WO | WO2005037345 | 4/2005 | |

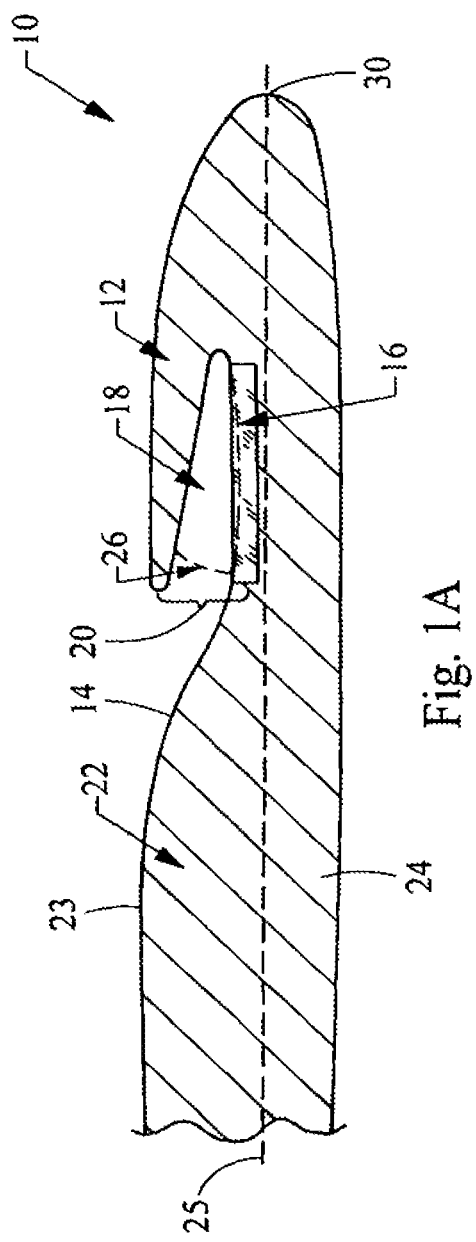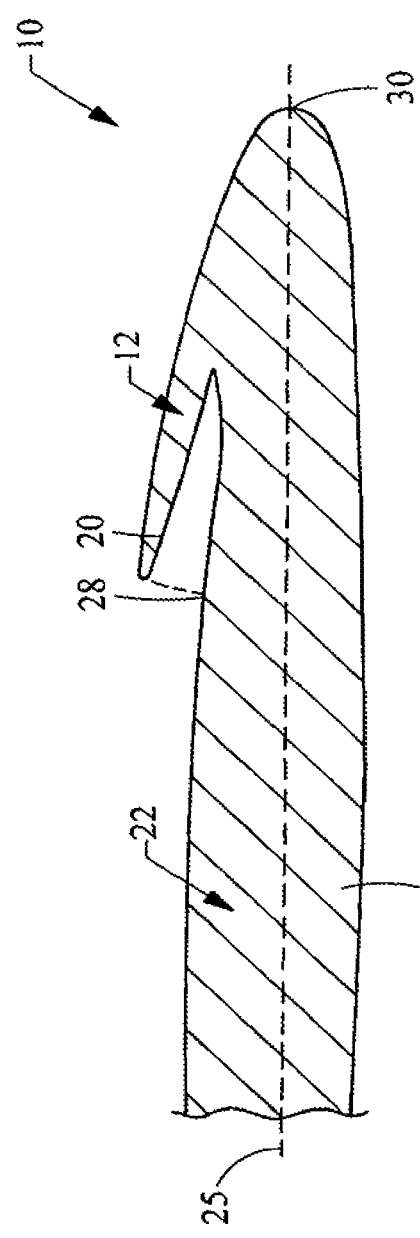
Fig. 1A
Fig. 1B

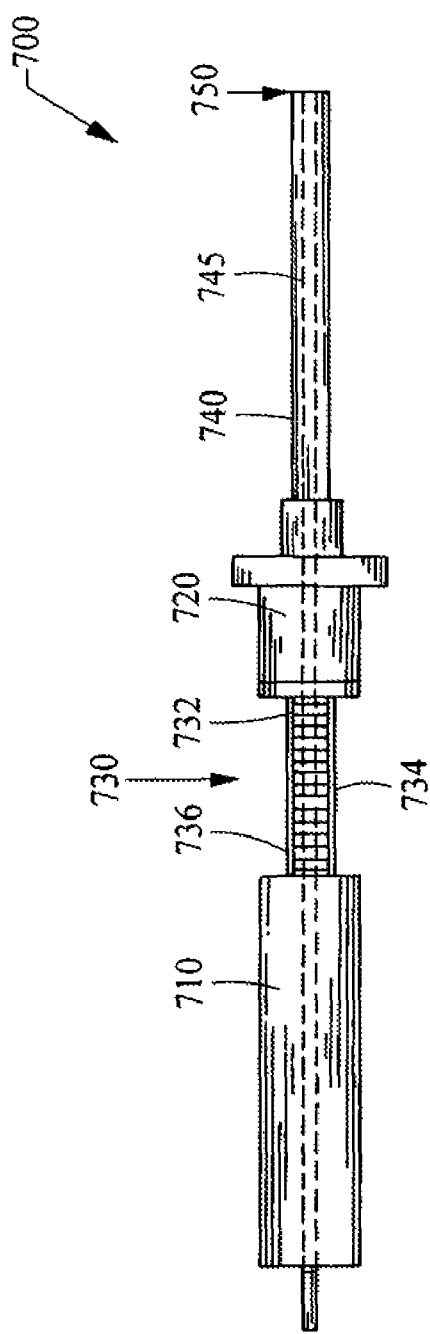
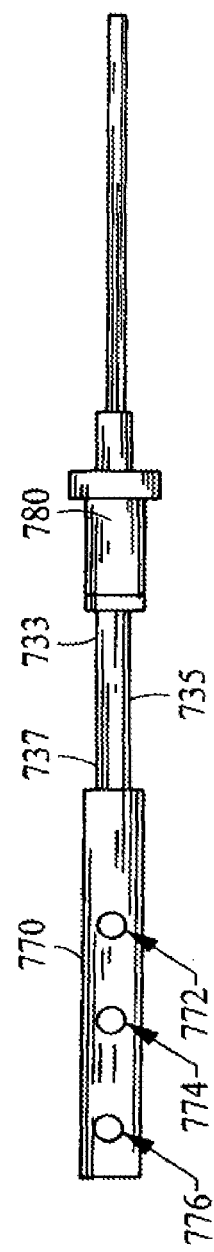
Fig. 7A
Fig. 7B

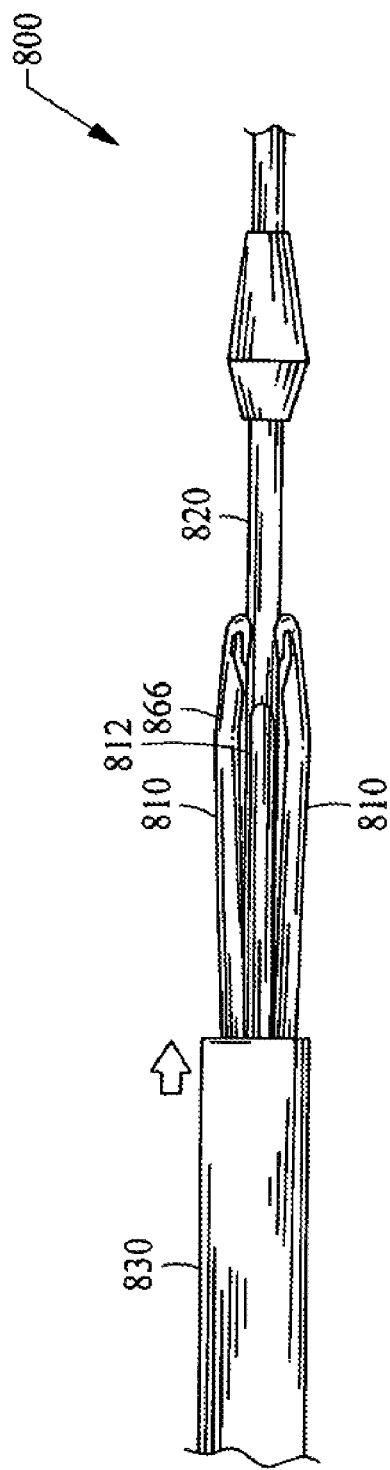
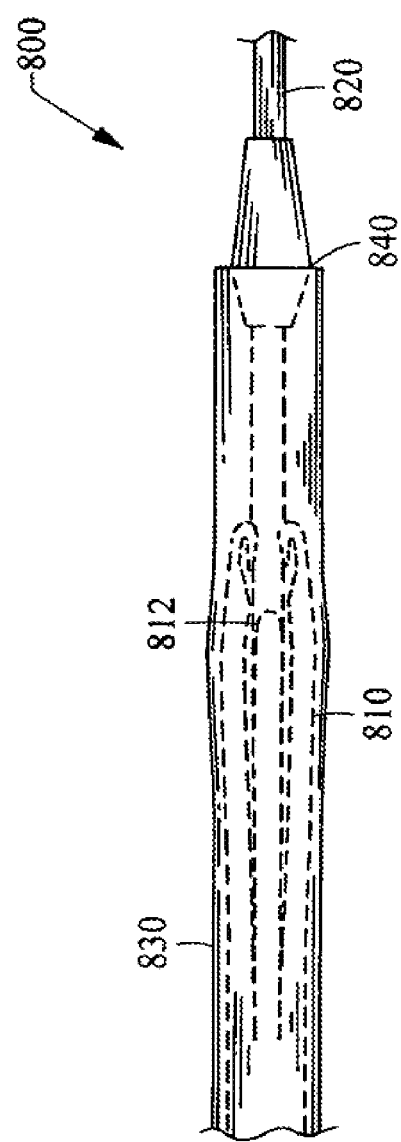
Fig. 8C
Fig. 8D

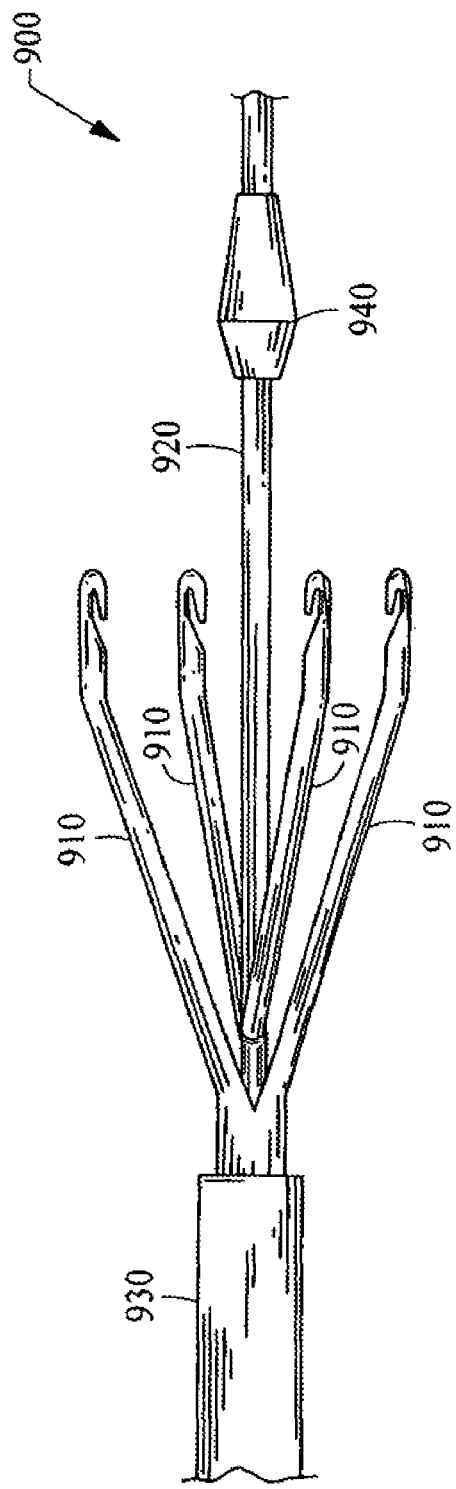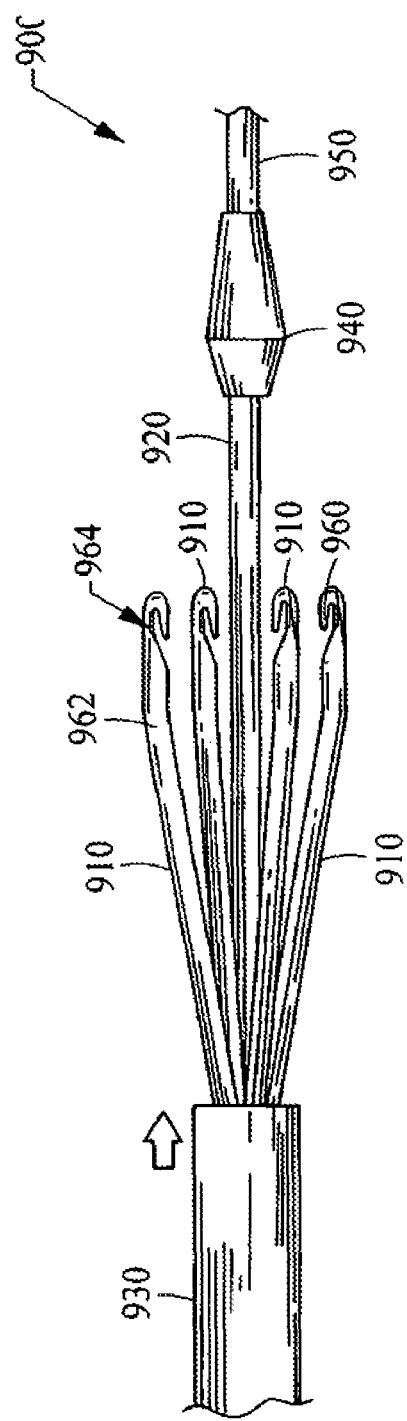
Fig. 9A
Fig. 9B

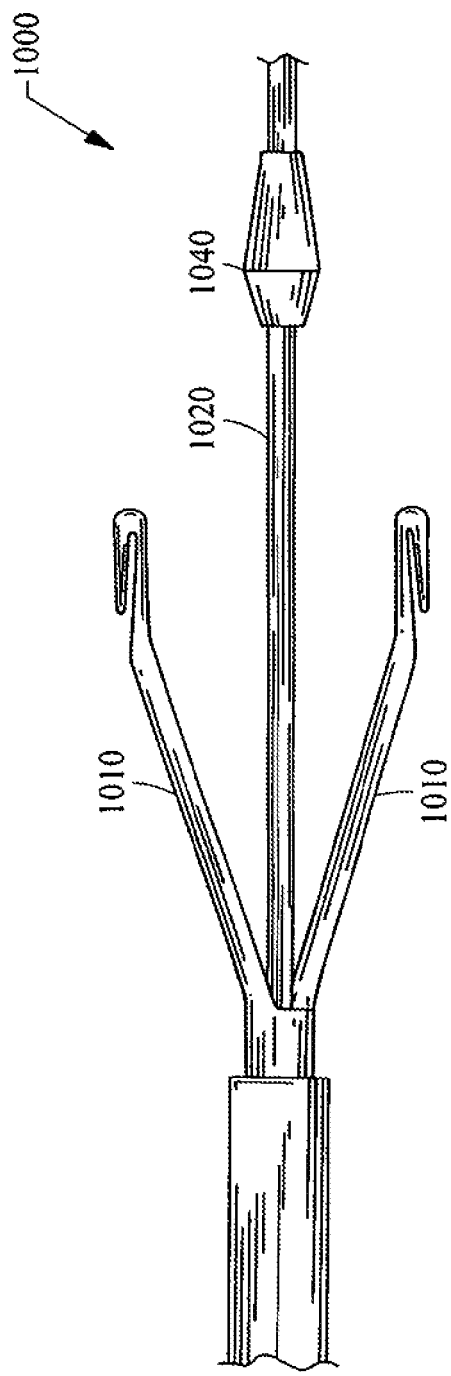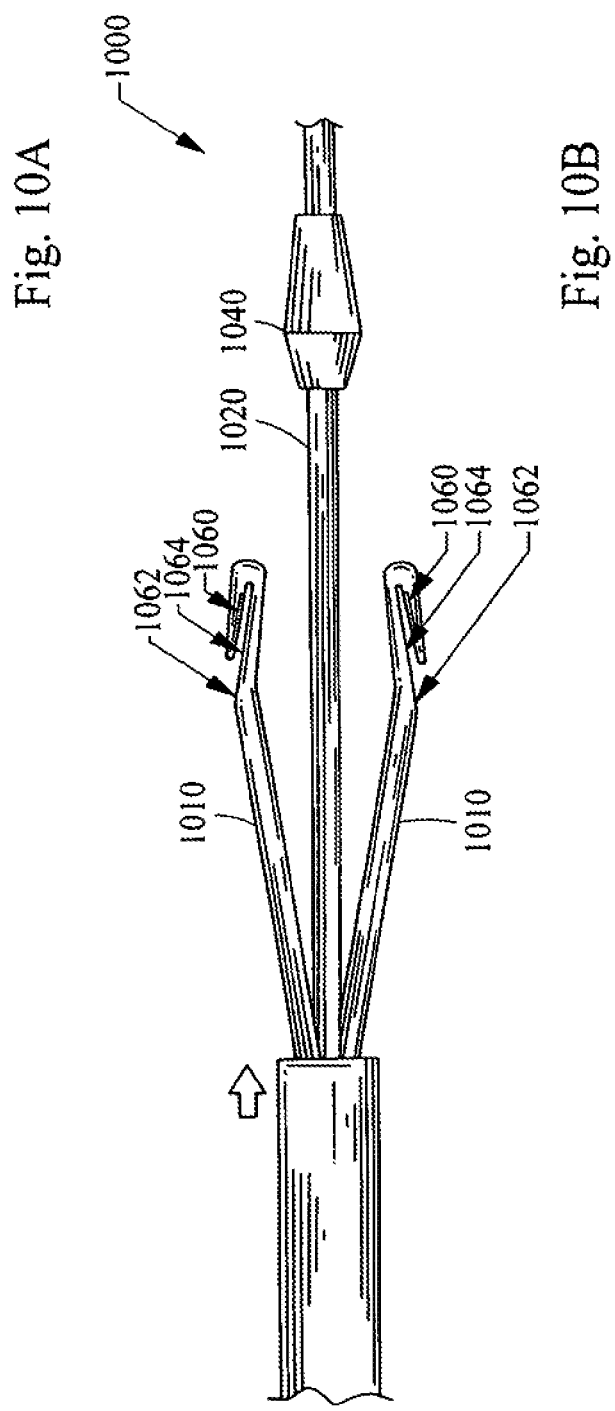
Fig. 10A
Fig. 10B

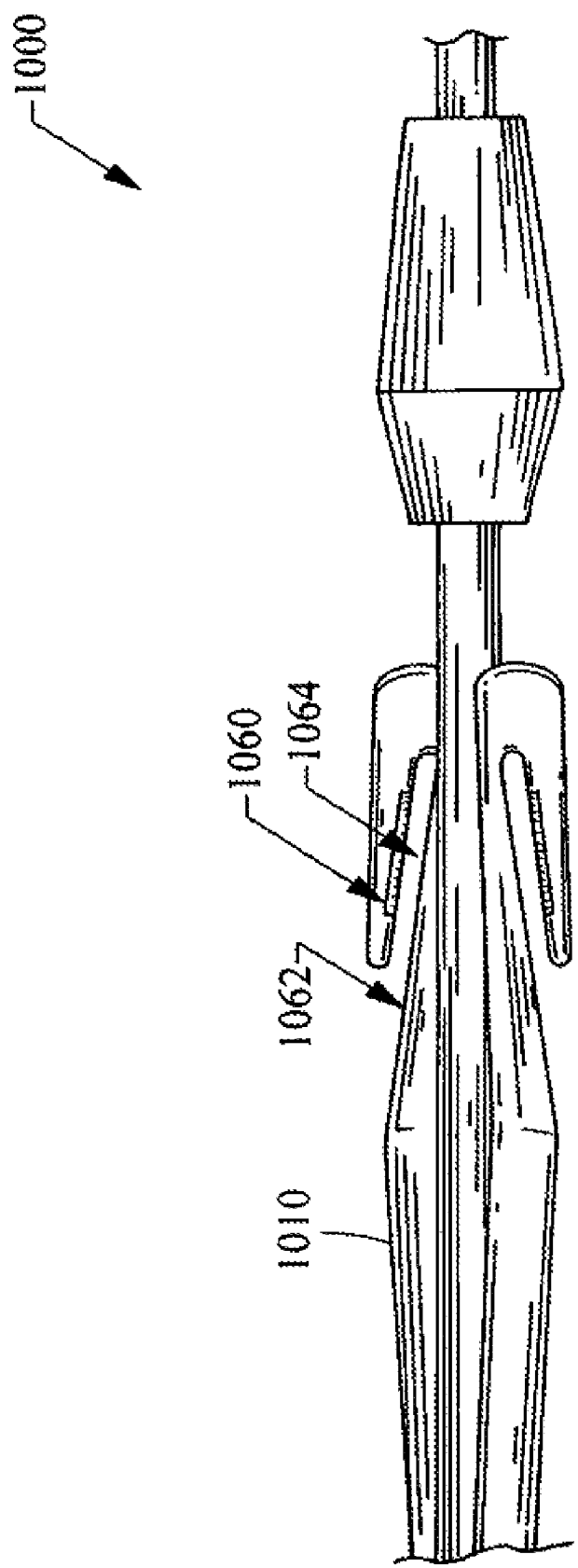

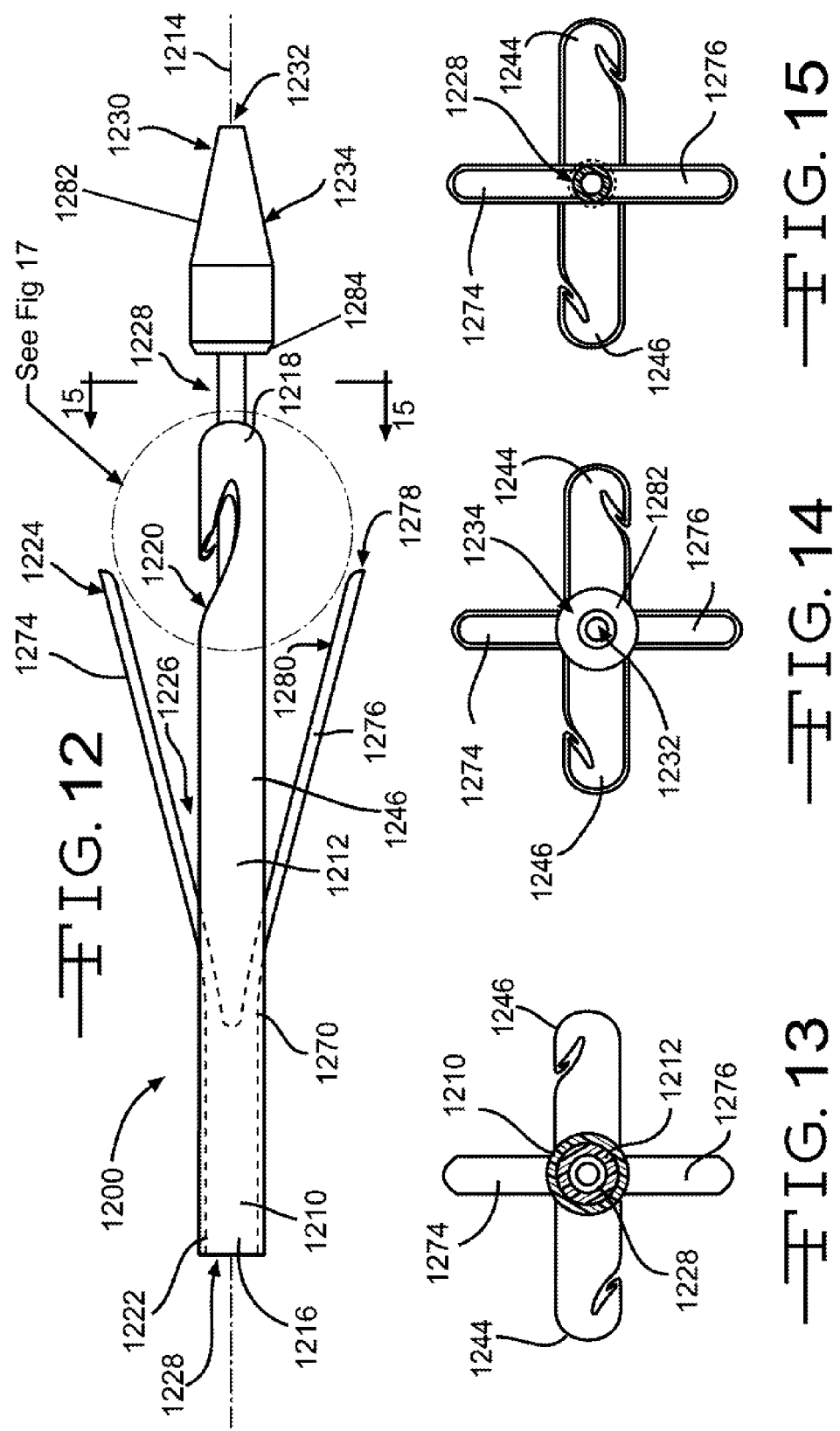

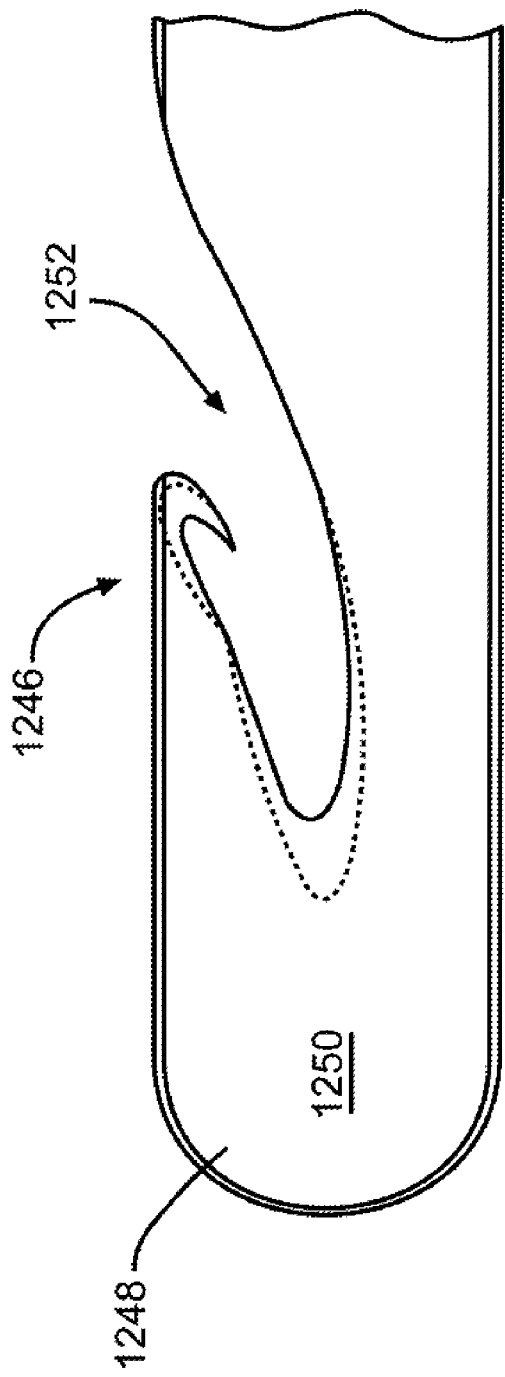
FIG. 18
FIG. 19
FIG. 20

VALVULOTOME DEVICE AND METHOD

CROSS REFERENCE TO RELATED APPLICATIONS

This Application is a continuation-in-part of U.S. patent application Ser. No. 11/070,130, filed on Feb. 28, 2005, now U.S. Pat. No. 7,717,930, which claims the benefit of U.S. Provisional Application Ser. No. 60/548,246, filed on Feb. 27, 2004, and U.S. Provisional Application Ser. No. 60/581,852, filed on Jun. 21, 2004. The entire contents of each of these related applications is incorporated into this disclosure by reference.

FIELD

The present invention relates to devices for removing or disabling valves within body vessels, such as venous valves. More particularly, the invention pertains to particular valvulotome devices and methods for using the same.

BACKGROUND

In mammalian veins, venous valves are positioned within portions of the vessel in the form of leaflets disposed annularly along the inside wall of the vein which open to permit blood flow toward the heart and close to prevent back flow. These venous valves open to permit the flow of fluid in the desired direction, and close upon a change in pressure, such as a transition from systole to diastole. When blood flows through the vein, the pressure forces the valve leaflets apart as they flex in the direction of blood flow and move toward the inside wall of the vessel, creating an opening in between for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. The competence of venous valves can be degraded or reduced if the leaflets do not adequately contact each other.

Disabling of incompetent venous valves can be performed for various reasons. For example, disabling of incompetent venous valves can be performed prior to implantation of a venous valve prosthesis. Venous valves may also be disabled within a section of vein used as a graft for surgical implantation at another site, where venous valves are often removed or disabled prior to implantation of the graft. Procedures such as in a coronary artery bypass grafting (CABG) commonly use vein segments with disabled or disrupted venous valves.

There are several procedures known in the art for disabling venous valves. Valvulotome devices are often used to render native venous valves incompetent. Several mechanical valvulotomes have been devised to date to cut valves in veins. The most common valvulotome in use is the mechanical valvulotome, which is an instrument with cutting edges specially designed to be passed into veins to cut the valves mechanically.

One disadvantage of the mechanical valvulotome is the possibility of injury to the walls of the vein. Moreover, there is the possibility that a valve could be missed since the valvulotome could slip past the valve. This potential problem is of major concern as it would lead to intraoperative angiograms and increased length of the primary surgical procedure.

Preferred valvulotome devices described herein have one or more cutting edges oriented in a manner that reduces potential injury to the walls of the vein. Furthermore, some embodiments provide valvulotome device embodiments comprising structural features adapted to slidably engage a venous valve leaflet. Related delivery devices and kits, as well as methods for using the same, are also provided by embodiments described herein.

SUMMARY

In some embodiments, a valvulotome device presenting a cutting edge that incisably engages a venous valve leaflet within a body vessel is provided. Preferably, at least a portion of the cutting edge is oriented substantially parallel to the longitudinal axis of the valvulotome device. More preferably, at least a portion of the cutting edge is oriented substantially parallel to the longitudinal axis of the body vessel when the cutting edge is deployed within a body vessel. Some embodiments provide valvulotome devices comprising surfaces configured to slidably engage a venous valve leaflet upon translation of the valvulotome device along the longitudinal axis of a body vessel.

In some embodiments, the valvulotome device comprises a means for capturing tissue within a body vessel. The valvulotome device preferably comprises a capturing structural feature, such as a leaflet engaging probe member.

In some embodiments, the valvulotome device comprises a means for guiding tissue in a body vessel toward the cutting edge. The valvulotome device preferably comprises a guiding structural feature, such as an angled surface.

Some valvulotome device embodiments provide a notch for slidably engaging a venous valve leaflet. In some embodiments, the notch perimeter can be defined by a leaflet engaging probe member, an angled surface or a cutting edge. In some embodiments, the leaflet engaging probe member can be angled with respect to the cutting edge.

The valvulotome device preferably comprises one or more valvulotome arms of variable lengths and dimensions. Preferably, one or more valvulotome arms present a cutting edge that incisably engages a venous valve leaflet within a body vessel while at least a portion of the cutting edge is oriented substantially parallel to the longitudinal axis of the valvulotome device, substantially parallel to the longitudinal axis of a body vessel lumen, or both. In some embodiments, the valvulotome device can further comprise valvulotome arms that do not present a cutting edge. Each valvulotome arm preferably comprises a proximal end fixed about a central radial position and a distal end comprising a cutting edge. The distal end is preferably moveable from a radially compressed position to an expanded position.

Preferably, the valvulotome arms are contoured to allow the device to open and close in a controlled fashion. The valvulotome arms can be contoured to facilitate movement between a radially-compressed delivery configuration and a radially-expanded deployed configuration. The valvulotome arm can have an angled or twisted conformation. Preferably, the angle of a valvulotome arm with respect to an interior guide wire can be correlated to the amount of translation required to deploy the valvulotome arm at a particular diameter. Angling of a portion of a valvulotome arm can also facilitate closure of the device in a compressed configuration. A portion of a valvulotome arm can be twisted to orient a leaflet-engaging probe member or cutting edge within a body vessel.

Some embodiments provide delivery systems comprising a valvulotome device. In some embodiments, the valvulotome device can be compressed to a delivery configuration that is suitable for intraluminal delivery into a body vessel, for example via a catheter. In some embodiments, the valvulotome device can be compressed and retained in a low-profile configuration suitable for translation through the lumen of a body vessel to a point of treatment with minimal disruption of or abrasion to the body vessel. For example, the valvulotome device can be compressed by a flexible outer sheath or ring. Preferably, the valvulotome device can be delivered using a guide wire. In some delivery system embodiments, the valvulotome device can be inserted within a tubular outer sheath that is inserted into the body lumen as part of a catheter-based delivery system.

A delivery system preferably comprises a means for monitoring the position or configuration of a valvulotome device, or any portion thereof, in a body vessel. In some embodiments, the valvulotome device further comprises a means for monitoring the position or configuration of the valvulotome device in a body vessel.

In some embodiments of the present invention, the valvulotome device or delivery system can be configured to deliver any suitable intraluminal medical device, such as a stent, an occluder, or a prosthetic venous valve.

Some embodiments provide methods for using a valvulotome device. One method comprises the step of inserting a valvulotome device into a body vessel. Also provided are methods where a valvulotome device is translated longitudinally (e.g., by sliding) within the body vessel, so that the valve capturing structural feature can mechanically engage a venous valve leaflet. In some methods, a delivery system can be employed to advance a valvulotome device to a first point of treatment (POT). Preferably, this step comprises advancing a delivery system that includes an outer sheath, a valvulotome device and an inner guide wire conduit through a body vessel. Alternatively, this step can comprise advancing a valvulotome device through a tube that has previously been inserted into the body vessel. At the POT, the valvulotome device can be deployed.

Some embodiments provide kits comprising a valvulotome device, including kits further comprising a delivery system.

BRIEF DESCRIPTION OF THE DRAWINGS

FIG. 1A is a first cross-sectional view of a first valvulotome device.

FIG. 1B is a second cross-sectional view of the first valvulotome device of FIG. 1A.

FIG. 7A depicts a proximal portion of a first delivery system.

FIG. 7B depicts a proximal portion of a second delivery system.

FIG. 8A, FIG. 8B, FIG. 8C and FIG. 8D depict a sixth valvulotome device.

FIG. 9A, FIG. 9B and FIG. 9C depict a seventh valvulotome device.

FIG. 10A, FIG. 10B and FIG. 10C depict an eighth valvulotome device.

FIG. 12 is a side view of a valvulotome device.

FIG. 13 is a proximal end view of the valvulotome device illustrated in FIG. 12.

FIG. 14 is a distal end view of the valvulotome device illustrated in FIG. 12.

FIG. 15 is a section view of the valvulotome device illustrated in FIG. 12, taken along line 15-15.

FIG. 18 is a bottom view of a valvulotome arm of the valvulotome device illustrated in FIGS. 12-16.

FIG. 19 is a sectional view of the valvulotome arm illustrated in FIG. 17, taken along line 19-19.

FIG. 20 is a sectional view of the valvulotome arm illustrated in FIG. 17, taken along line 20-20.

DETAILED DESCRIPTION OF EMBODIMENTS

Figure 1C:
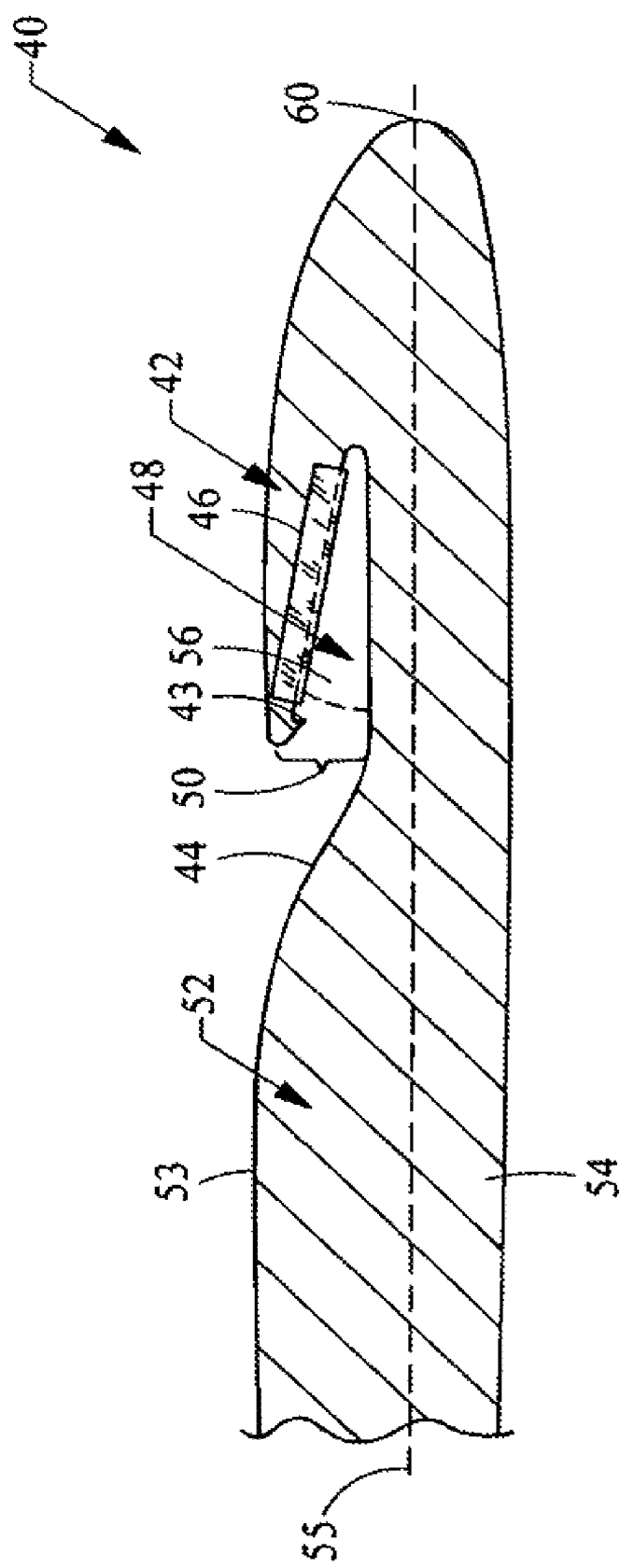
FIG. 1C is a cross-sectional view of a second valvulotome device.

The following provides a detailed description of some embodiments of the invention, for example, as illustrated by the drawings. The description is not intended to limit the invention in any manner, but rather serves to enable those skilled in the art to make and use the invention. As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The recitation of "about" or "substantially" used with reference to a quantity, such as an angle, includes variations in the recited quantity that are equivalent to the quantity recited, for instance an amount that is insubstantially different from a recited quantity for an intended purpose or function.

Preferably, valvulotome devices provided herein are adapted for intraluminal use within a body vessel and methods for their use. More preferably, the valvulotome devices provide a cutting edge for incising tissue within a body vessel. Preferably, the cutting edge can incise a venous valve leaflet. For example, the valvulotome device preferably presents a cutting edge that incisably engages a venous valve leaflet within a body vessel while at least a portion of the cutting edge is oriented substantially parallel to the longitudinal axis of a body vessel lumen. Orientation of the valvulotome device can be monitored using any suitable means. Examples of suitable means include radiopaque markers on the valvulotome device or delivery device, indicia on the delivery device, or emission of a signal by the valvulotome device or the delivery device.

As used herein "incisably engage" means to interlock with so that the motion of an incisably-engaged surface is constrained by an engaging surface. Under suitable conditions, further movement of the engaging surface may result in cutting of the engaged surface. For example, a cutting surface "incisably engaging" a tissue surface within a vein refers to a tissue surface positioned in any orientation with respect to a cutting surface so that the tissue surface can be cut by the cutting surface, for example by motion of the cutting surface relative to the tissue surface. A venous valve leaflet positioned across a cutting surface of a notch in a valvulotome arm is one example of an incisably-engaged surface. "Incisable engagement" does not require that the cutting surface actually cut into the first surface, but only that an engaged surface is positioned with respect to the engaging surface in a manner that allows for cutting of the engaged surface upon movement of the cutting surface.

A "cutting edge" refers to any surface of the valvulotome that is adapted to cut into a tissue material, such as a venous valve leaflet. For example, a cutting edge can refer to a sharpened or serrated edge, a heated or cooled surface, a vibrating surface, or a chemically-treated portion of any surface. The cutting edge can extend along any suitable portion of the valvulotome body. Some valvulotome devices comprise multiple separate cutting edges. Preferably, a cutting edge is located along portions of the perimeter of a notch structure, such as portions of a leaflet engaging probe member, portions of an angled surface, portions between an angled surface and a leaflet engaging probe member, or any combination thereof.

Valvulotome devices preferably comprise means for capturing tissue within a body vessel. Preferably, the valvulotome devices are adapted to capture venous valve leaflet tissue or portions of the vessel wall. Means for capturing tissue include, for example, any structural design of the valvulotome device, selection of materials forming the valvulotome device, coatings on the valvulotome device or modification of the valvulotome device materials that desirably promote the capture of tissue within a body vessel. Preferably, tissue is captured to incisable engage the tissue against a cutting edge. In certain aspects, means for capturing tissue can include portions of the surface of the valvulotome device coated with an adhesive, portions of the valvulotome device that are heated or cooled, serrated, angled, bent, perforated, sharpened or roughened surfaces of the valvulotome device, portions of the valvulotome device coated with biologically active materials that promote capturing tissue within a body vessel, or any combination of two or more of these aspects used in combination in a valvulotome device.

Preferably, valvulotome devices provide structural features configured to capture a venous valve leaflet within a body vessel. In one aspect, a valvulotome device comprises one or more surfaces configured to slidably engage a venous valve leaflet upon translation of the valvulotome device along the longitudinal axis of a body vessel. When the valvulotome device is translated longitudinally (e.g., by sliding) within the body vessel, a valve capturing structural feature can mechanically engage a venous valve leaflet. For instance, a capturing feature can be a probe or protrusion that contacts and guides tissue radially inwardly toward a cutting edge upon translation of the capturing feature along the longitudinal axis of the body vessel lumen.

Further provided in some aspects are valvulotome devices comprising means for guiding tissue toward a cutting edge. Means for guiding tissue include, for example, any structural design of the valvulotome device, selection of materials forming the valvulotome device, coatings on the valvulotome device or modification of the valvulotome device materials that desirably promote guiding tissue within a body vessel toward one or more cutting edges. The guiding of tissue can be performed in any suitable manner. For instance, tissue can be guided mechanically by relative movement of the guiding surface with respect to the tissue effective to slide the tissue toward a cutting edge. Tissue can also be guided by a guiding structural feature that modifies the flow of fluid in the body vessel so as to direct fluid flow in a manner that directs a portion of the tissue toward a cutting edge.

Preferably, the valvulotome device comprises a guiding structural feature in communication with one or more capturing structures, one or more cutting edges, or both a capturing structure and a cutting edge. Preferably, the guiding structural feature cooperates with a means for capturing tissue, for example to entrain tissue toward a cutting edge. In one aspect, a guiding structural feature can be a curved surface positioned in communication with a capturing feature and a cutting edge. Movement of the curved surface relative to the tissue slides the tissue toward the cutting edge, where it can be incisably engaged. In one aspect, the capture feature, the guiding feature and the cutting edge are formed from a single continuous notch or slit in a valvulotome arm. One example of a capture feature is a portion of the valvulotome surface adjacent to and angled with respect to the cutting edge, where the cutting edge is oriented substantially parallel to the vessel wall.

More preferably, the valvulotome device comprises a capturing structural feature that is a leaflet engaging probe member; or a guiding structural feature that is an angled surface; as well as the cutting edge. In a valvulotome device comprising both a probe member and an angled surface, the leaflet engaging probe member can be oriented in the same plane as the angled surface, or the leaflet engaging probe member can be oriented out of plane with respect to the angled surface.

In some aspects, one or more portions of the material of the valvulotome device, or any portion thereof, can have greater radial resilience, stiffness or compliance than other portions of the device. For example, portions of a cutting edge or a guiding structure can have increased flexibility compared with the capturing feature. In other aspects, a capturing feature can have greater flexibility than a guiding structure or a cutting edge.

In a first embodiment, a valvulotome device comprises one or more cutting edges positioned near the distal portion of the valvulotome device. Preferred distal valvulotome device structures permit incisable engagement of tissue in a body vessel by the cutting edge. Various aspects of the first embodiment are illustrated with respect to certain exemplary valvulotome device structures. The first embodiment is not limited to the exemplary valvulotome device structures presented, but also includes any combinations of the features illustrated therein.

A first example of a valvulotome device 10 is shown in FIG. 1A and FIG. 1B. FIG. 1A shows a first cross-sectional view of the valvulotome device 10. The valvulotome device 10 has a body 22 having a first body side 23, an opposing second body side 24, and a rounded distal body surface 30. The body 22 can have any suitable cross-sectional configuration. In one aspect, the cross section of the body 22 is curved or U-shaped. In another aspect, the body 22 has a rectangular or circular cross-sectional shape. A longitudinal axis 25 is shown in both FIG. 1A and FIG. 1B. FIG. 1B shows a second cross-sectional view of the valvulotome device 10 rotated 90.degree. around the longitudinal axis 25 to show the second body side 24.

The valvulotome body 22 comprises a capturing means that is a capturing structural feature, shown as a leaflet engaging probe member 12; a guiding means that is a guiding structural feature, shown as an angled surface 14; and a cutting edge 16. The cutting edge 16 can be a sharpened surface or any surface that will desirably cut tissue that is incisably engaged. One or more cutting edges can be positioned along any portion of the notch 18. Other structures corresponding to the capturing structural feature, the guiding structural feature or the cutting edge are provided in other valvulotome structures. The perimeter 20 of a notch 18 of the structure shown in FIG. 1A extends along the cutting edge 16 and portions of the angled surface 14 and one side of the leaflet engaging probe member 12. The cutting edge 16 can extend along any portion of the valvulotome body 25, along portions of the notch perimeter 20, portions of the leaflet engaging probe member 12, or any combination thereof. The geometry of the perimeter 20 of the notch 18 can be varied. In FIG. 1A, the angled surface 14 and the cutting edge 16 are in contiguous communication, and, together with the leaflet engaging probe member 12, define a notch in a body 18 of the valvulotome device, which is shown as a curvilinear surface.

The leaflet engaging probe member 12 can be oriented in any suitable direction and angle with respect to the rest of the valvulotome device 10. In the valvulotome 10 illustrated in FIG. 1A and FIG. 1B, the leaflet engaging probe member 12 is oriented at a first angle 26 with respect to the cutting surface 16 and at a second angle 28 with respect to the portion of the body 22 that is substantially parallel to the longitudinal axis 25 of the valvulotome device 10. The first angle 26 and the second angle 28 can be illustrated with respect to FIG. 1A and FIG. 1B, respectively. In FIG. 1A, a first cross-sectional view of the valvulotome device 10 shows the leaflet engaging probe member 12 defining a portion of the notch 18 that is positioned at the first angle 26 with respect to the cutting edge 16. The second cross-sectional view of the valvulotome device 10 shown in FIG. 1B is obtained by a 90.degree. rotation of the first cross-sectional view of FIG. 1A around the longitudinal axis 25 so that the second body side 24 is substantially co-planar with the second cross-sectional view. As shown in FIG. 1B, a portion of the notch perimeter 20 along one side of a leaflet engaging probe member 12 defines a second angle 28 with respect to the portion of the body 22 that is substantially parallel to the longitudinal axis 25. The first angle 26 and the second angle 28 can be fixed by forming the leaflet engaging probe member 12 from a rigid material, or variable by forming the leaflet engaging probe member 12 from a flexible material. Preferably, the notch perimeter 20 defines a first angle 26 that is between about 0.degree. and 30.degree. The leaflet engaging probe member 12 is optionally oriented at a second angle 28 that is between about 0.degree. and 30.degree. Preferably, the second angle 28 is either 0.degree., or, when present, is preferably between about 5.degree. and 25.degree., and more preferably between about 7.degree. and 20.degree. The first angle 26 and the second angle 28 can be selected to optimize the ease of engagement of tissue in a body vessel.

In operation, the body 22 of the valvulotome device can be translated toward a venous valve along the interior of a vein, with the surface of the body 22 or the outer body edge 24 in contact with the interior vessel wall. In operation, as the body 22 is translated toward a leaflet of the venous valve, the leaflet can be incisably engaged by a cutting edge 16 (for example by entraining the leaflet between the leaflet engaging probe member 12 and the angled surface 14, thereby guiding the leaflet toward the cutting edge 16). Once the cutting edge 16 incisably engages the leaflet, further movement of the valvulotome, including translation or twisting of the cutting surface 16 with respect to the leaflet, can incise the leaflet to compromise or disable the venous valve function.

FIG. 1C is a cross-sectional view of a second example of a valvulotome device 40. The valvulotome device 40 has a body 52 having a first body side 53, an opposing second body side 54, and a rounded distal body surface 60. The body 52 can have any suitable cross-sectional configuration. In one aspect, the cross section of the body 52 is curved or "U"-shaped. In another aspect, the body 52 has a rectangular or circular cross-sectional shape. A longitudinal axis 55 is also shown.

The valvulotome body 52 comprises a means for capturing tissue that is a structural feature, shown as a leaflet engaging probe member 42 having a barb 43 that facilitates capture of tissue in a body vessel; a guiding means that is a guiding structural feature, shown as an angled surface 44; and a cutting edge 46. The cutting edge 46 is a sharpened portion of the leaflet engaging probe member 42. The barb 43 is positioned between the cutting edge 46 and the tip of the leaflet engaging probe member 42. The perimeter 50 of a notch 48 of the valvulotome device 40 extends along the cutting edge 46 and one side of the leaflet engaging probe member 42. In FIG. 1C, the angled surface 44 and the cutting edge 46 are not in contiguous communication. A portion of the leaflet engaging probe member 42 defines the notch 48 of the valvulotome device. The notch perimeter 50 forms a first angle 56 between the cutting surface and the portion of the first body side 53 opposite the cutting surface 46 and substantially parallel to the longitudinal axis 55.

Figure 1D:
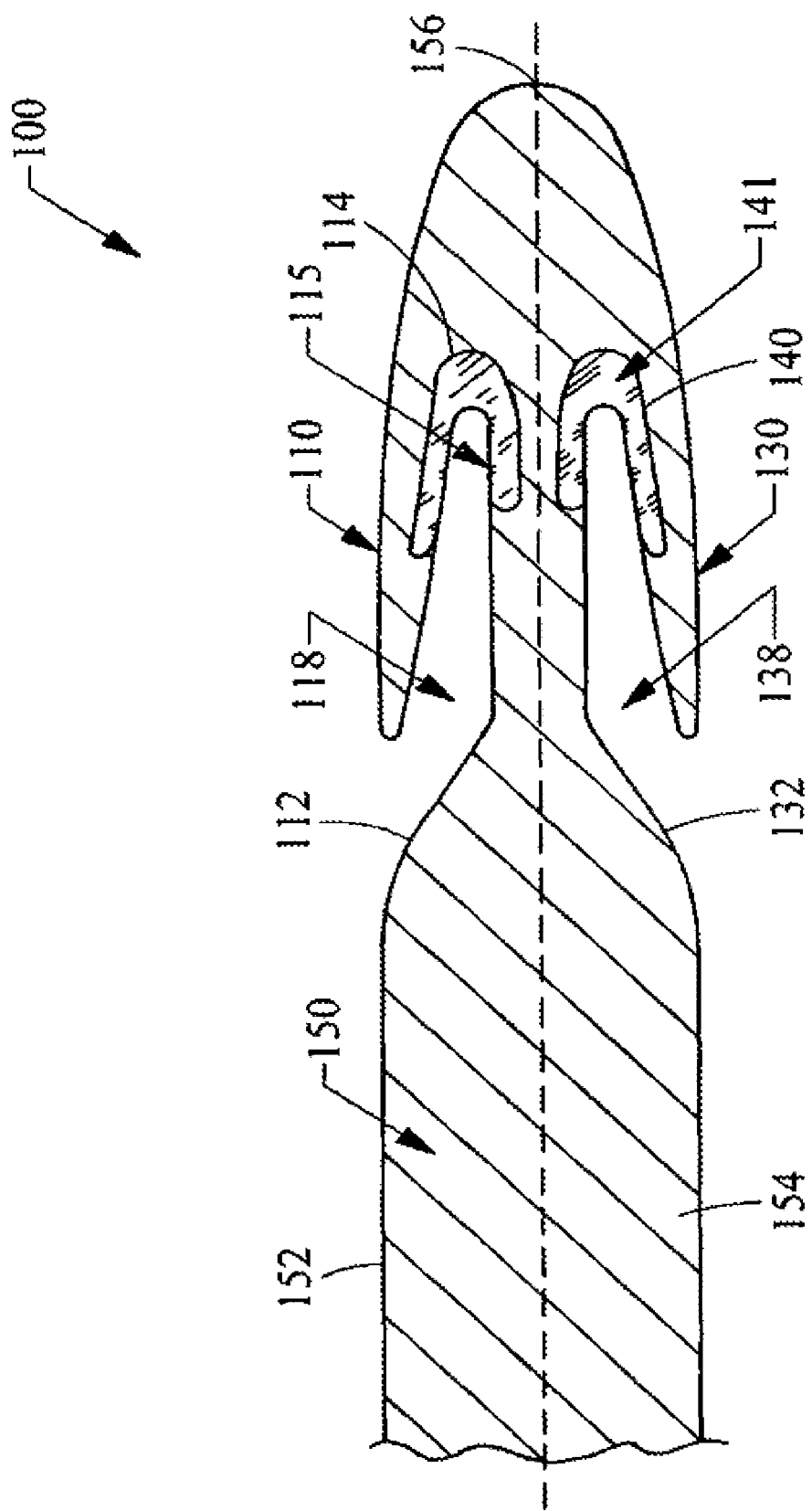
FIG. 1D is a cross-sectional view of a third valvulotome device.

A valvulotome device can optionally comprise multiple cutting edges, or cutting edges that extend outside of a notch structure. FIG. 1D is a cross-sectional view of a third example of a valvulotome device 100 that comprises multiple cutting edges. The valvulotome device 100 has a body 150 having a first body side 152, an opposing second body side 154, and a rounded distal body surface 156. The body 150 can have any suitable cross-sectional configuration. In one aspect, the cross section of the body 150 is curved or "U"-shaped. In another aspect, the body 150 has a rectangular or circular cross-sectional shape.

The valvulotome body 150 comprises a first leaflet engaging probe member 110 and a second leaflet engaging probe member 130. The valvulotome body 150 further comprises a guiding means that is a pair of guiding structural features, shown as a first angled surface 112 and a second angled surface 132. The valvulotome device 100 also comprises a first cutting edge 114 and a second cutting edge 140. The first cutting edge 114 and the second cutting edge 140 are sharpened edges along the first notch 118 and the second notch 138, respectively. A segment 115 of the first cutting edge 114 between the first angled surface 112 and the first leaflet engaging probe member 110 is substantially parallel to the longitudinal axis of the valvulotome device 100. Similarly, a segment 141 of the second cutting edge 140 between the second angled surface 132 and the second leaflet engaging probe member 130 is substantially parallel to the longitudinal axis of the valvulotome device 100.

The valvulotome device 100 comprises several structural features that cooperatively function to capture tissue in a body vessel, for example to incisably engage a venous valve leaflet by relative motion of the body of the valvulotome with respect to the venous valve leaflet. In one aspect, the position and configuration of the first notch 118 provides a means for capturing tissue. In another aspect, the position and configuration of the second notch 138 provides a means for capturing tissue. Another aspect the combination, configuration or relative orientation or position of the first notch 118 and the second notch 138 provides a means for capturing tissue. A portion of the first cutting edge 114 and the first leaflet engaging probe member 110 in combination with portion of the first body side 152 define the perimeter of the first notch 118 of the valvulotome device. Similarly, a portion of the second cutting edge 140 and the second leaflet engaging probe member 130 in combination with portion of the second body side 154 define the perimeter of the second notch 138 of the valvulotome device.

Figure 1E:
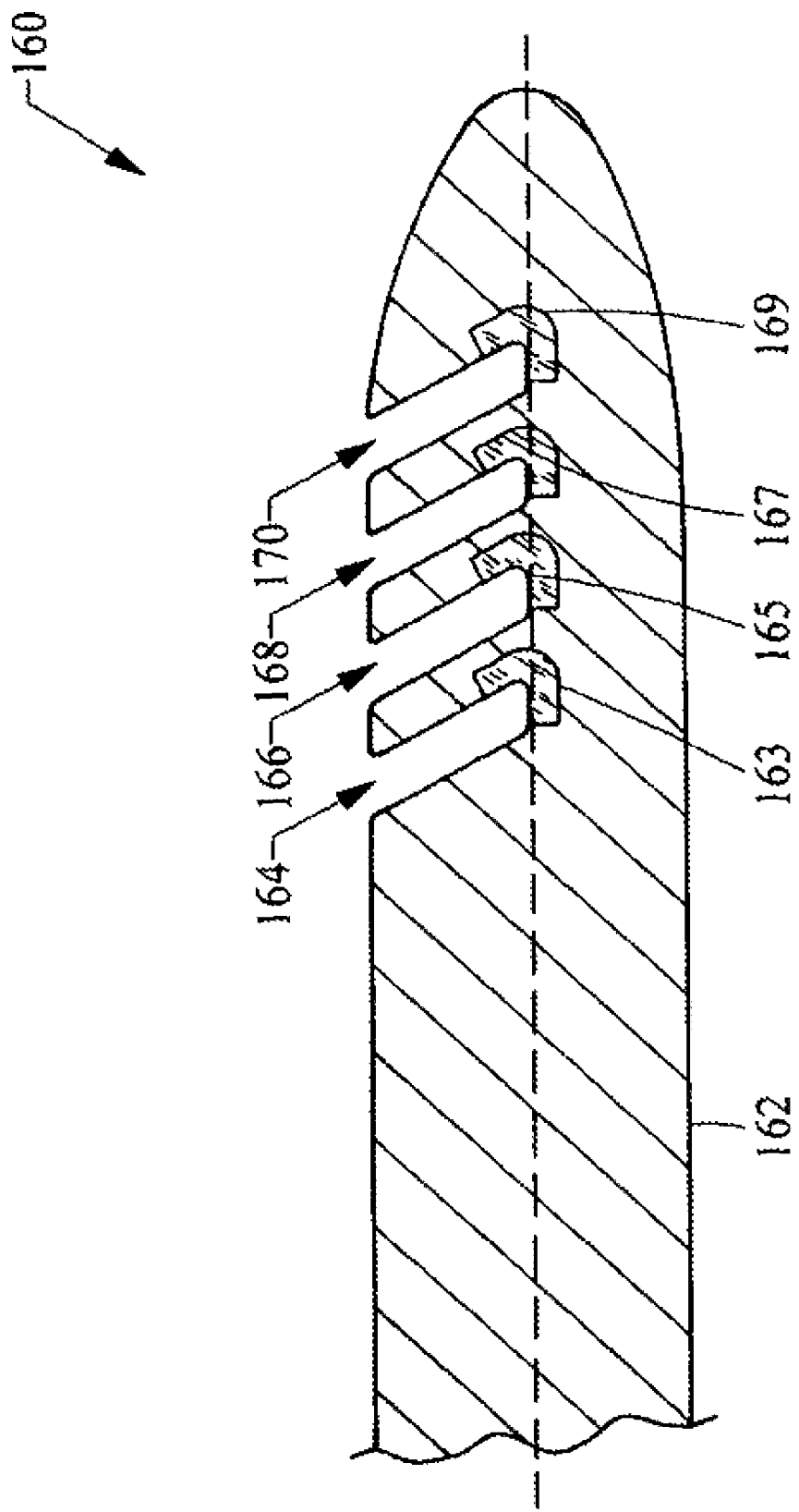
FIG. 1E is a cross-sectional view of a fourth valvulotome device.

A valvulotome device can optionally comprise multiple notches configured to capture tissue. For example, multiple probes with cutting surfaces can be distributed along the length of a valvulotome device at any suitable angle and relative spacing or orientation to define a plurality of notches. FIG. 1E is a cross-sectional view of a fourth example of a valvulotome device 160 that comprises multiple notches with cutting edges. The valvulotome device 160 has a body 162 having a plurality of notches. A first notch 164 comprises a first cutting edge 163, a second notch 166 comprises a second cutting edge 165, a third notch 168 comprises a third cutting edge 167, and a fourth notch 170 comprises a fourth cutting edge 169. Preferably, at least a portion of each cutting edge is oriented substantially parallel to a wall of a body vessel when the valvulotome device incisably engages tissue.

In a second embodiment, the valvulotome device can further comprise one or more valvulotome arms of any suitable length, dimension and spatial orientation with respect to one another. Preferably, the valvulotome arms comprise an elongated structure having a proximal end attached to a delivery device, such as the outer surface of an interior guide wire conduit. Preferably, the valvulotome arms comprise an elongated structure having a distal end that is radially moveable between a radially compact delivery configuration and a radially expanded configuration within a body vessel. More preferably, the distal end of a valvulotome arm comprises a cutting edge positioned near the distal end and is adapted to incisably engage tissue when the valvulotome arm is in the radially-expanded configuration. Most preferably, the distal portion of one or more valvulotome arms comprises a valvulotome structure of the first embodiment.

One or more valvulotome arms preferably present a cutting edge that incisably engages a venous valve leaflet within a body vessel. More preferably, at least a portion of the cutting edge is oriented substantially parallel to the longitudinal axis of the valvulotome arm, the longitudinal axis of a body vessel lumen, or both. Preferably, the valvulotome can have 2, 3, 4, 5, 6, 7, 8, 9, 10, 11, 12, 13, 14, 15 or 16 valvulotome arms. Some preferred valvulotome devices comprises 2, 4, or 6 valvulotome arms. Another preferred valvulotome device includes two or more valvulotome arms arrayed in a radially-symmetric fashion about the longitudinal axis of the valvulotome device. For instance, two valvulotome arms can be positioned opposite each other, three valvulotome arms can be arranged at about 120.degree. from each other, and four valvulotome arms can be arranged about 90.degree. apart from each other. Similar arrangements of other numbers of valvulotome arms are similarly provided. In some valvulotome devices, one or more valvulotome arms can have one or more cutting edges. A valvulotome device can optionally comprise one or more valvulotome arms with cutting edges, as well as one or more valvulotome arms without cutting edges. Valvulotome arms can facilitate orientation and use of the valvulotome device, for example by dilating a body vessel or centering the valvulotome device in a body vessel, as well as providing one or more cutting edges to incisably engage tissue. Some preferred valvulotome devices have an even number of valvulotome arms. Valvulotome devices with two or more valvulotome arms preferably have the valvulotome arms arranged radially around an interior longitudinal axis. Preferably, valvulotome devices comprise pairs of valvulotome arms opposably-arranged across from one another. One or more valvulotome arms can comprise self expanding material. However, valvulotome devices having valvulotome arms without self expanding material are also provided. For example, valvulotome arms can be expanded by a balloon or an outwardly-biased spring at the proximal end of a valvulotome arm.

Figure 2:
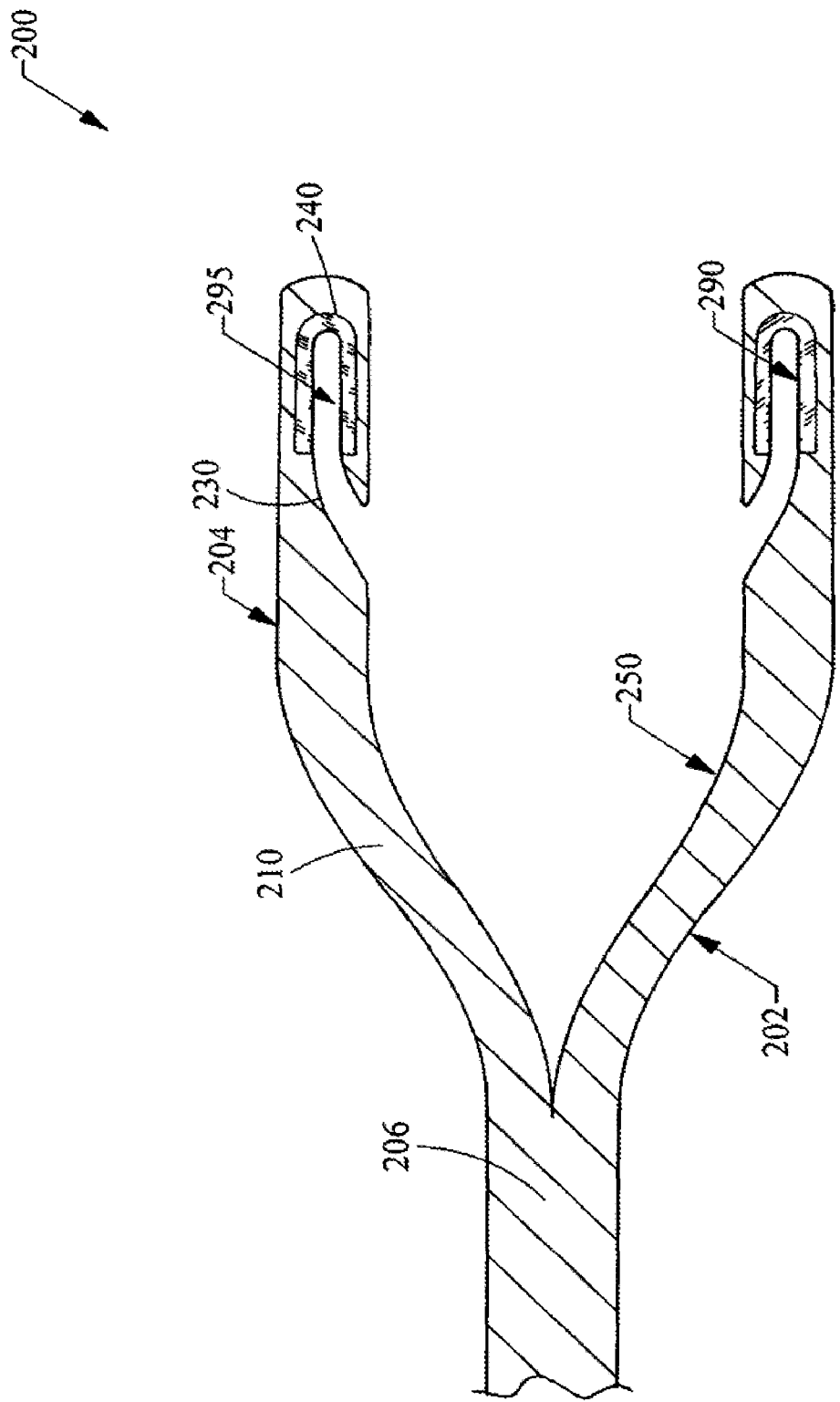
FIG. 2 depicts a fifth valvulotome device comprising two valvulotome arms.

The valvulotome device can further comprise a valvulotome arm with a concave U-shaped cross section comprising a capturing structural feature, a guiding feature, or both. Preferably, the valvulotome device can comprise two or more valvulotome arms. FIG. 2 illustrates a first example of a valvulotome device 200 of the second embodiment. The valvulotome device 200 includes a first valvulotome arm 210 and a second valvulotome arm 250 joined at a first end (not shown) in a V-shape. The valvulotome device 200 comprises a first leaflet engaging probe member 220; a first angled surface 230 and a first cutting edge 240, which are shown in contiguous communication. Together with each leaflet engaging probe member, each angled surface and cutting edge define separate notches (not shown) in the first body 295 and the second body 290, respectively. While the bodies of the valvulotome arms are shown with U-shaped cross sections in FIG. 2, valvulotome arms having bodies with other cross-sectional dimensions and configurations can also be used. For example, the valvulotome arms can be more or less curved along the length of the valvulotome arm body, and the valvulotome arms can have cross-sections that are curved to varying degrees, including crescent-shaped or rectangular cross sections. The valvulotome arms can also have a circular cross section.

A valvulotome device can be configured around an inner guide wire conduit formed from any suitable material, for example, a biocompatible polymer. A valvulotome arm preferably closes around a portion of the inner guide wire conduit in a compressed configuration and the inner guide wire conduit can house a guidewire. Preferably, the proximal end of each valvulotome arm is fixedly attached to an inner guide wire conduit. When fully deployed, the proximal end of a valvulotome arm can extend any suitable distance from an internal guide wire conduit. For some applications, such as treatment of human veins, the outside radius measured between the center of the internal guide wire conduit and the proximal end of the valvulotome arms is between about 1.00 mm and about 10.00 mm, and preferably about 2, 3, 4, 5, or 6 mm, any increment of 1.00, 0.50 or 0.25 mm therebetween, or more. For treatment of animal veins, such as bovine veins, the radius is typically in the range of 10.0-20.0 mm, any increment of 1.00, 0.50 or 0.25 mm therebetween, or more.

Figure 3:
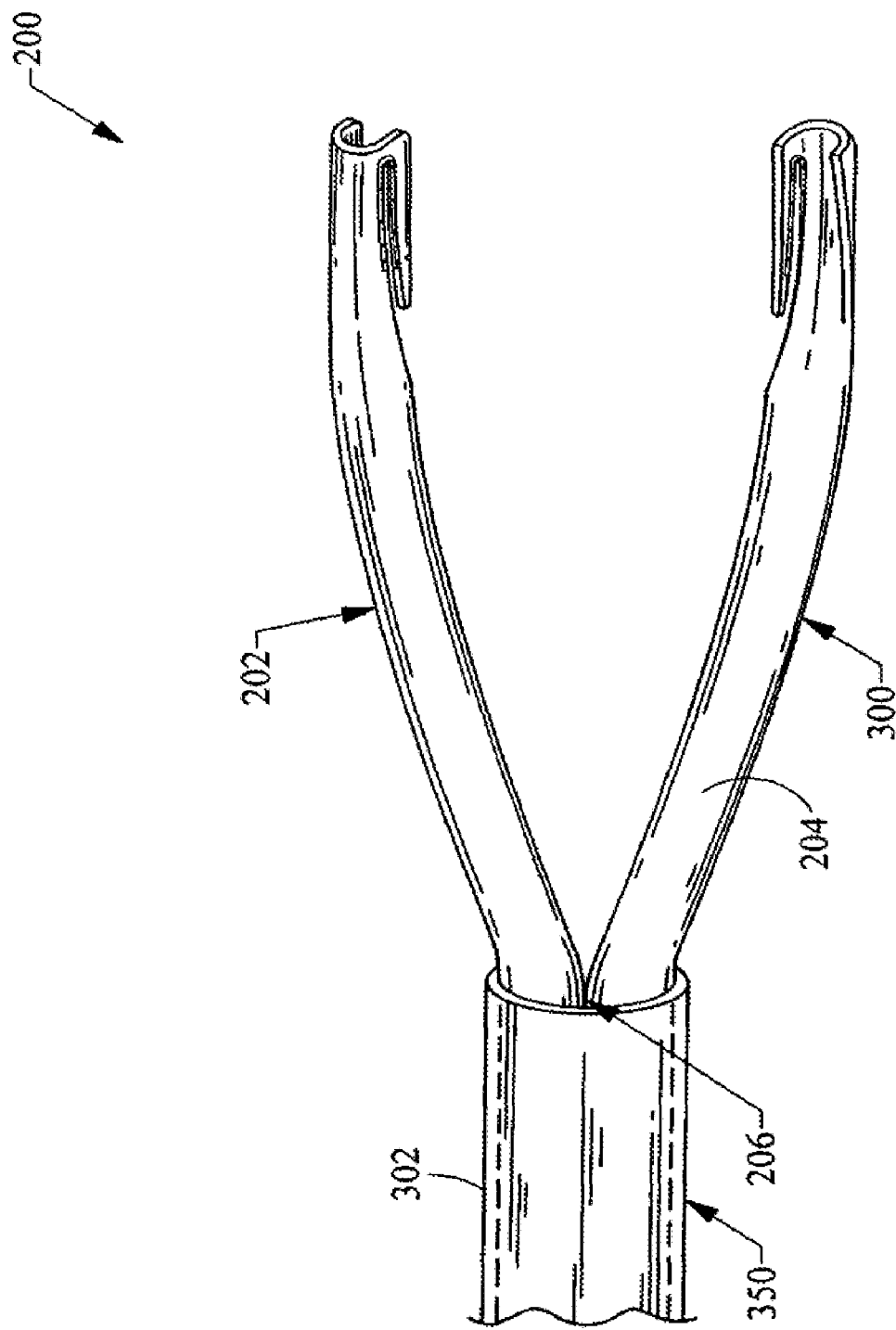
FIG. 3 depicts the fifth valvulotome device of FIG. 2 in combination with an outer sheath.
Figure 4:
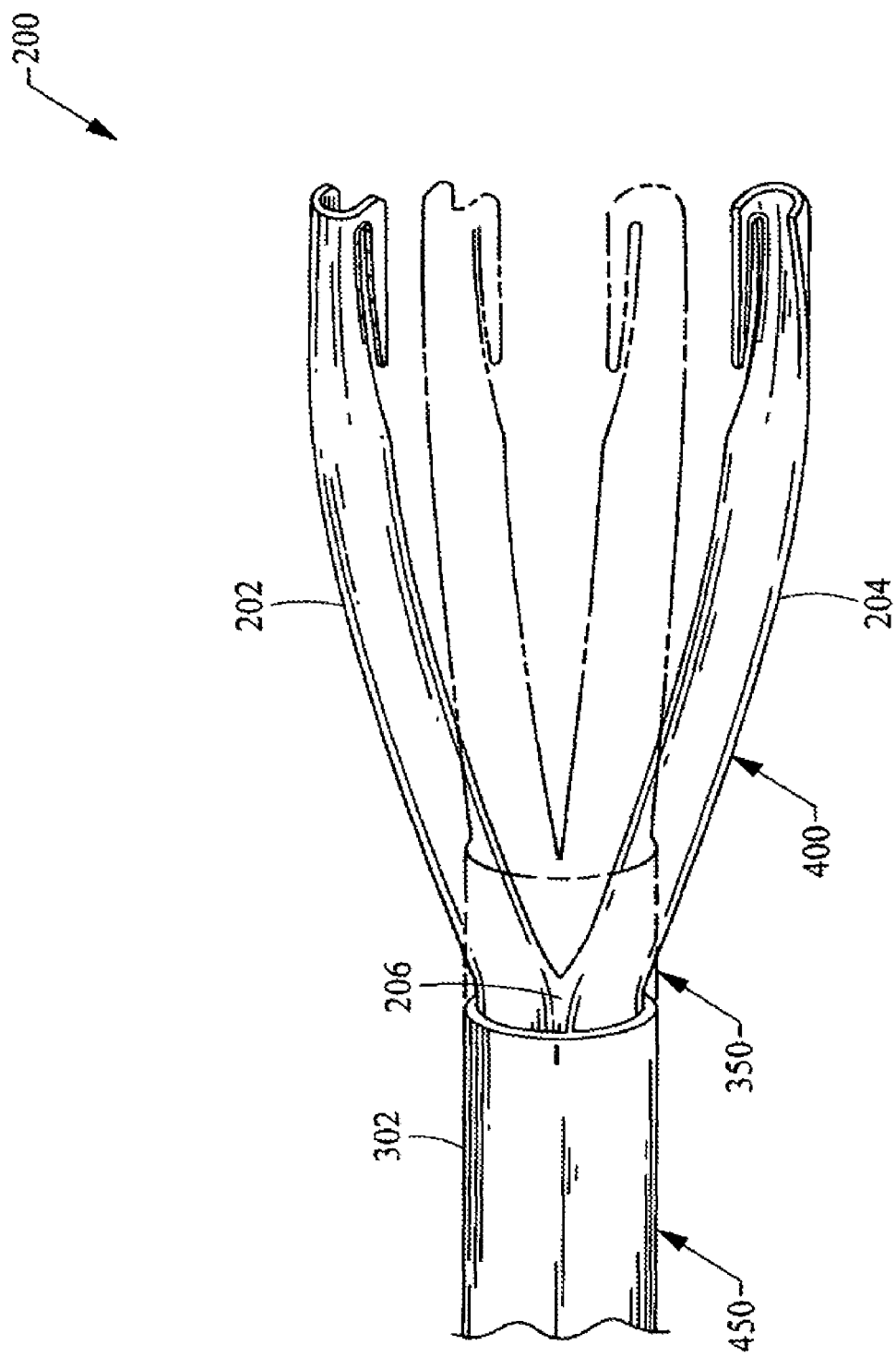
FIG. 4 depicts the fifth valvulotome device of FIG. 2 and FIG. 3 in combination with an outer sheath.

In another aspect, the valvulotome arm can have an angled or twisted conformation. By introducing bends, twists or angles to the configuration of a valvulotome arm, the orientation of the valvulotome device within a body vessel or a cutting edge attached to the valvulotome arm can be adjusted. Preferably, the angle of a valvulotome arm with respect to an interior guide wire can be correlated to the amount of translation required to deploy the valvulotome arm at a particular diameter. Angling of a portion of a valvulotome arm can also facilitate closure of the device in a compressed configuration. In one aspect, a portion of a valvulotome arm can be twisted to orient a leaflet engaging probe member or cutting edge within a body vessel. In FIG. 2, the valvulotome device 200 comprises a first valvulotome arm 202 and a second valvulotome arm 204, both of which have a bent configuration. In FIG. 3 and FIG. 4, the movement of the outer sheath 302 in relation to the first valvulotome arm 202 and the second valvulotome arm 204 results in angle of each valvulotome arm can be adjusted.

Preferably, the valvulotome device has a low-profile configuration. For example, in one aspect, a valvulotome device comprises multiple valvulotome arms that are adapted to radially retract to form a low-profile, compressed configuration. In one preferred aspect, the length of two or more adjacent valvulotome arms can be staggered to facilitate compact folding from an expanded to a compressed configuration.

The valvulotome device can be self centering within a body vessel. Preferably, radially-symmetric valvulotome arms can facilitate self centering of the valvulotome device in a body vessel. For example, two, three or four valvulotome arms can be disposed in a radially-symmetric fashion to facilitate centering of the device. In another aspect, the valvulotome device maintains the valvulotome arms at a constant radial angle with respect to an interior guide wire upon deployment, for example, by using a Touhy-Borst adapter. In some aspects, the valvulotome device can comprise a first valvulotome arm having a cutting edge and a second valvulotome arm without a cutting edge that facilitates orientation of the valvulotome device within a body vessel. Different valvulotome arms can have different compliance against a body vessel so as to facilitate orientation of the valvulotome device within a body vessel.

The valvulotome device can be formed from any suitable material, or combinations of materials. In one aspect, one or more valvulotome arms comprising a cutting edge of the valvulotome device are formed by laser cutting NITINOL® tubing.

Preferably, the valvulotome device is self expanding. Upon compression, self expanding valvulotome devices can expand toward their pre-compression geometry. In some aspects, a self expanding valvulotome device can be compressed into a low-profile delivery configuration and then constrained within a delivery system for delivery to a point of treatment in the lumen of a body vessel. At the point of treatment, the self expanding valvulotome device can be released and allowed to subsequently expand to another configuration.

In certain embodiments, the valvulotome device is formed partially or completely of alloys such as Nickel-Titanium alloys (NiTi), including those sold under the tradename NITINOL® or TINEL®. The valvulotome can also be made in whole or in part from other materials including cobalt-chromium; stainless steel (including 302-304, 316, and 400 series); elgiloy; phynox; MP35N; cobalt-chromium alloys; diamond-like carbon; tungsten; a nickel-iron-chromium alloy such as those sold under the tradename ICONEL®; aluminum; titanium; or other titanium alloys; or platinum, gold or other noble metals. The valvulotome device can also be coated with a lubricant or a bioactive coating, such as an antibiotic optionally combined with a polymer carrier.

Preferably, valvulotome devices comprise self expanding valvulotome arms comprising superelastic alloys. Alloys having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. For example, superelastic characteristics can generally allow a NiTi valvulotome to be deformed by collapsing the valvulotome and creating stress which causes the NiTi to reversibly change to the martensitic phase. The valvulotome can be restrained in the deformed condition inside an outer sheath typically to facilitate the insertion into a patient's body, with such deformation causing the isothermal phase transformation. Once within the body lumen, the restraint of the outer sheath on the valvulotome can be removed, thereby reducing the stress thereon so that the superelastic valvulotome returns toward its original undeformed shape through isothermal transformation back to the austenitic phase.

The shape memory effect allows a NiTi structure to be deformed to facilitate its insertion into a body lumen or cavity, and then heated within the body so that the structure returns to its original, set shape.

Shape memory effect can be imparted to an alloy useful in constructing a self expanding valvulotome by heating the nickel-titanium metal to a temperature above which the transformation from the martensitic phase to the austenitic phase can be complete; i.e., a temperature above which the austenitic phase can be stable. The shape of the metal during this heat treatment can be the shape "remembered." The heat-treated metal can be cooled to a temperature at which the martensitic phase can be stable, causing the austenitic phase to transform to the martensitic phase. The metal in the martensitic phase can be then plastically deformed, e.g., to facilitate the entry thereof into a patient's body. Subsequent heating of the deformed martensitic phase to a temperature above the martensitic to austenitic transformation temperature causes the deformed martensitic phase to transform to the austenitic phase. During this phase, transformation of the metal reverts back towards its original shape.

The recovery or transition temperature may be altered by making minor variations in the composition of the metal and in processing the material. In developing the correct composition, biological temperature compatibility must be determined in order to select the correct transition temperature. In other words, when the valvulotome can be heated, it must not be so hot that it can be incompatible with the surrounding body tissue. Other shape memory materials may also be utilized, such as, but not limited to, irradiated memory polymers such as autocrosslinkable high-density polyethylene (HD-PEX). Shape memory alloys are known in the art and are discussed in, for example, "Shape Memory Alloys," Scientific American, Vol. 281, pp. 74-82 (November 1979), incorporated herein by reference.

Preferably, the valvulotome arms can be moved between a radially-compressed delivery configuration and a radially-expanded configuration in a gradual, controllable manner. Valvulotome arms can be contoured to facilitate radial compression and housing of the valvulotome arm in a radially compressed configuration. Preferably, an annular outer sheath is positioned around one or more radially self expanding valvulotome arms so as to compress the valvulotome arms into the radially-compressed delivery configuration. By controlling the longitudinal translation of the outer sheath with respect to one or more of the enclosed valvulotome arms, the radial position of the enclosed valvulotome arms can be controlled. Movement of the outer sheath from the proximal toward the distal end of the enclosed valvulotome arms results in radial expansion of the valvulotome arms, and movement of the outer sheath in the opposite direction radially compresses the valvulotome arms. In one aspect, the valvulotome arms can be contoured to facilitate movement between a low-profile, radially-compressed delivery configuration and a radially-expanded deployed configuration.

In general, an outer sheath can be a flexible, kink-resistant introducer sheath, as described in U.S. Pat. No. 5,380,304, which is incorporated in its entirety herein by reference. The outer sheath preferably comprises one or more radiopaque regions for imaging the outer sheath within a body vessel.

FIG. 3 and FIG. 4 illustrate the controlled expansion of the valvulotome device 200, where the valvulotome device is made from a self-expanding NiTi alloy material. The valvulotome device 200 comprises a first valvulotome arm 202 and a second valvulotome arm 204, each having a U-shaped cross section, and are joined together at a common proximal end 206. FIG. 3 shows the valvulotome device 200 in a partially-expanded state 300. An outer sheath 302 in the position 350 encloses the common proximal end 206 of the valvulotome device 200 and constrains the valvulotome arms from attaining a fully radially-expanded configuration. In FIG. 4, the outer sheath 302 is translated in the direction of the proximal end of the valvulotome arms, exposing the common proximal end 206 and allowing the first valvulotome arm 202 and the second valvulotome arm 204 to achieve a fully radially-expanded configuration 400. The two valvulotome arms are spaced progressively farther apart as they expand apart from each other, as the outer sheath 302 is moved in the proximal direction with respect to the valvulotome arms 202, 204. For comparison with the fully expanded configuration 400, the position of the outer sheath 350 and the valvulotome arms in the partially-expanded state 300 is also indicated in FIG. 4.

In a third embodiment, delivery systems are provided. A delivery system preferably comprises a valvulotome device in a radially-compressed configuration within an outer sheath. The valvulotome device can be compressed to a delivery configuration that is suitable for intraluminal delivery into a body vessel, for example via a catheter. In some aspects, the valvulotome device can be compressed and retained in a low-profile configuration suitable for translation through the lumen of a body vessel to a point of treatment with minimal disruption of or abrasion to the body vessel. For example, the valvulotome device can be compressed by a flexible outer sheath or ring. In some delivery systems, the valvulotome device can be inserted within a tubular outer sheath that is inserted into the body lumen as part of a catheter-based delivery system.

Preferred delivery devices also comprise an inner guide wire conduit. The valvulotome device is preferably annularly configured around an interior guide wire tube conduit. The interior guide wire conduit preferably is adapted to house a guide wire to direct the valvulotome device and a delivery catheter to a point of treatment through the lumen of a body vessel. Preferably, the proximal ends of each arm of the valvulotome device is fixedly attached to an inner guide wire conduit. The inner guide wire conduit can be made of any suitable material, such as a polyamide polymer material. The valvulotome device can also be disposed adjacent to an inner guide wire conduit, or be delivered separately from the inner guide wire conduit.

In one aspect, the valvulotome device can be delivered using an "over-the-wire" technique that employs a guide wire to deliver the valvulotome device through a body vessel. In this aspect, the blood vessel into which a valvulotome device is to be inserted can be punctured, a thin guide wire generally being about twice the length of the distal lumen (i.e., the channel whose end is furthest away from the operator), which ends centrally relative to the round cross section at the tip of the catheter, is advanced in the blood vessel via the puncture cannule. After the guide wire has been advanced, the puncture cannule is removed by pulling back via the wire. A dilator catheter is then advanced in the vessel via the guide wire. A dilator catheter is preferably a relatively robust and rigid single-lumen catheter made of a plastic material and having a distal tip tapering to the diameter of the guide wire. The purpose of the dilator catheter is to expand the puncture channel through skin, fat and muscle tissue and the blood vessel wall to the diameter of the catheter. After expansion, the dilator catheter is removed, the guide wire remains in the blood vessel with the distal tip. The free proximal (i.e. closest to the operator) end of the guide wire is then inserted into the tip of the catheter also tapered toward the guide wire diameter and advanced into the blood vessel via the guide wire. As soon as the catheter is correctly positioned, the guide wire is pulled out of the so-called distal lumen; thus, the distal lumen of the catheter is available for other uses, such as delivery of a valvulotome device.

Figure 5:
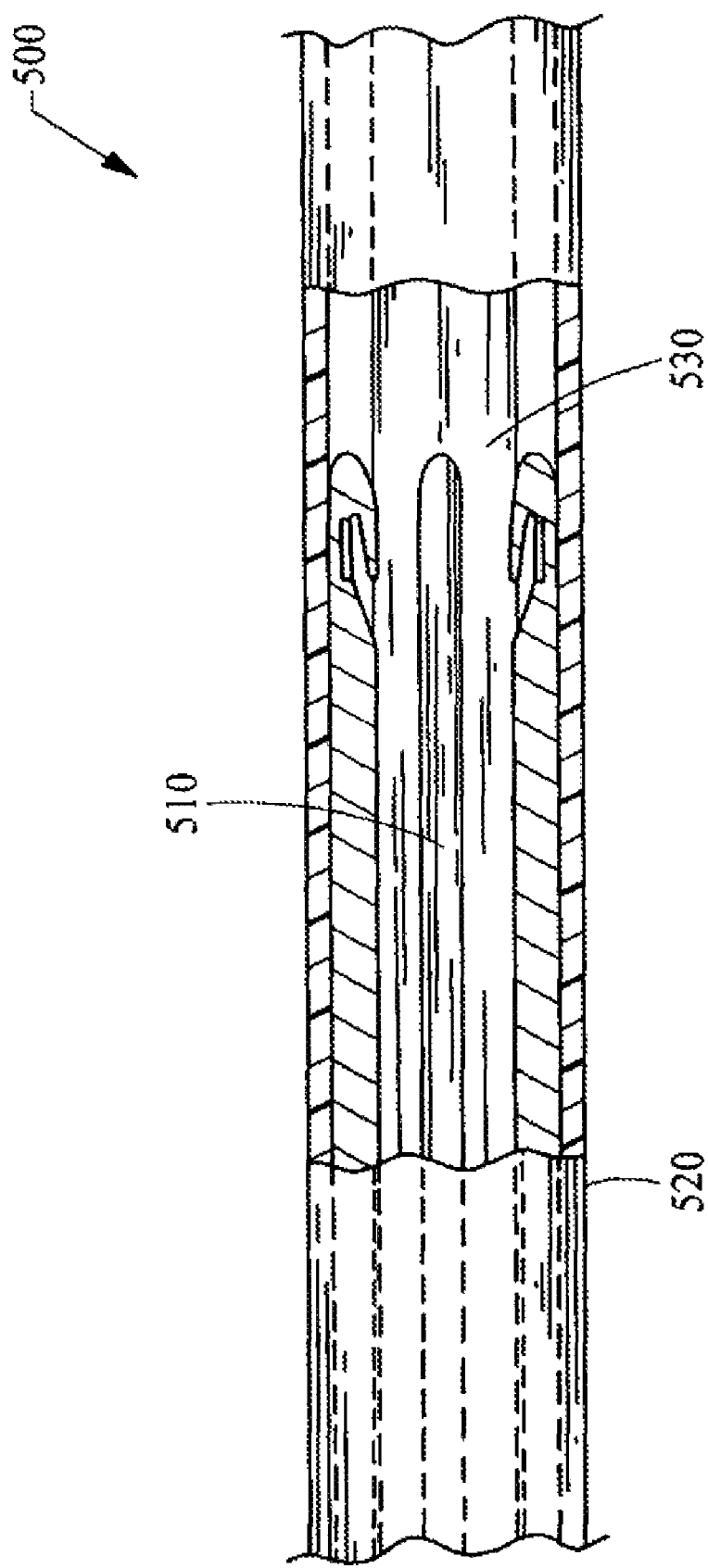
FIG. 5 depicts a distal portion of a first delivery system.
Figure 6:
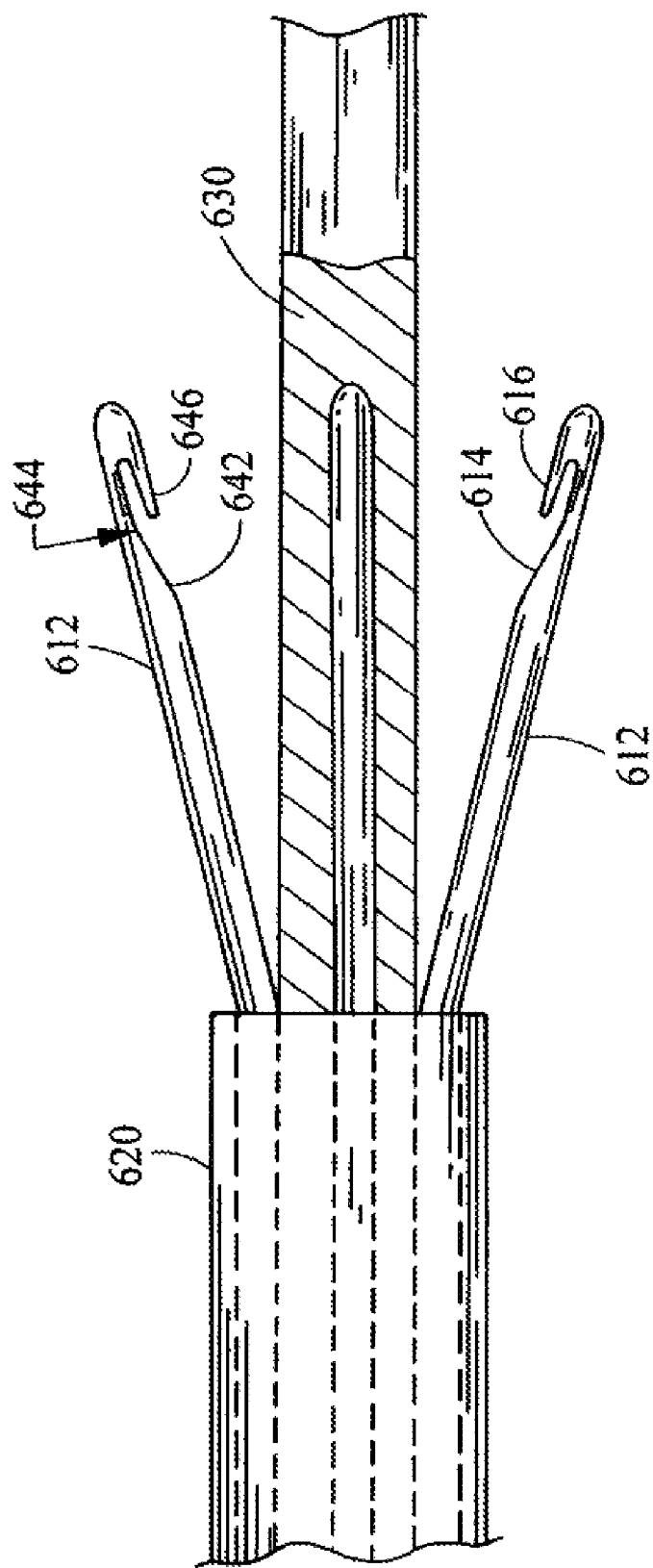
FIG. 6 depicts a distal portion of the delivery system of FIG. 5.

FIG. 5 shows a portion of a delivery system 500 comprising a flexible outer sheath 520 enclosing a self expanding valvulotome device 510 in a compressed delivery conformation and an inner guide wire conduit 530. FIG. 6 shows a delivery system 600 substantially similar to the delivery system 500 of FIG. 5, except that the outer sheath 620 has been retracted from the valvulotome device 610. When the outer sheath 620 is retracted away from the valvulotome device 610, the plurality of valvulotome arms 612 of the self-expanding valvulotome device 610 expand away from the compressed formation toward a deployment configuration. Each valvulotome arm 612 comprises a cutting edge, an angled surface and a leaflet engaging probe member that together define a notch. For example, a first leaflet engaging probe member 616, a second leaflet engaging probe member 646, a first angled surface 614, a second angled surface 642, and a second cutting edge 644 are all labeled in FIG. 6. Also shown in FIG. 6 are a flexible outer sheath 620, which has been retracted to deploy the valvulotome device 610, and an inner guide wire conduit 630.

Preferably, the delivery system provides for the controlled radial deployment of one or more valvulotome arms within a body vessel. For example, a valvulotome comprising self expanding valvulotome arms enclosed in an outer sheath can be deployed by the relative motion between the outer sheath and the self expanding valvulotome arms. For example, as shown in FIG. 7A, a proximal portion of a delivery device 700 is shown, having a distal end 750 in communication with a self expanding valvulotome device (not shown) that is enclosed in an outer sheath within a body vessel. Movement of the proximal handle 710 of the delivery device 700 moves the outer sheath (not shown) relative to the valvulotome device within a body vessel. The proximal handle 710 can be translated in relation to the distal handle 720, which is attached to a section of tubular conduit 740. Movement of the outer sheath 740 relative to an interior guide wire conduit 745 radially expands or contracts the valvulotome arms of the valvulotome device, thereby adjusting the position of one or more cutting edges of the valvulotome device.

The valvulotome device preferably comprises a means for monitoring the position or the position and configuration of a valvulotome device, or any portion thereof, in a body vessel. For example, the valvulotome device can comprise a radiopaque marker. Radiopaque markers can be incorporated in or placed on any suitable portion of the valvulotome device or a delivery system, such as on the outer sheath, the inner guide wire conduit or a radiopaque tip distal to the outer sheath.

Incorporation of a radiopaque material can be useful, for example, to facilitate tracking and positioning of the valvulotome device. The radiopaque material may be added in any fabrication method or absorbed into or sprayed onto the surface of part or all of the medical device. The degree of radiopacity contrast can be altered by the type and amount of material incorporated into the device. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. Radiopacity is typically determined by fluoroscope or x-ray film.

In a preferred aspect, the valvulotome delivery device comprises a tip, an outer sheath comprising a radiopaque material, or both. The tip can be positioned distal to one or more valvulotome arms in a compressed state. When the radiopaque material is incorporated at the distal end of the outer sheath and in the tip, the deployment of the valvulotome arms between the two points can be correlated to the separation of the radiopaque markers in the tip and the outer sheath. .vertline.Radiopaque markers on the valvulotome device or the delivery device can also be used in combination with indicia on the delivery device corresponding to the position or orientation of the valvulotome device or portions thereof. For instance, a delivery device handle can include markings correlated to the radial expansion of valvulotome device within a body vessel. . . vertline.

The valvulotome delivery device also preferably comprises a means for monitoring the position and configuration of a valvulotome device, or any portion thereof, in a body vessel. For example, the position of the cutting edge, or degree of radial expansion of one or more valvulotome arms of the valvulotome can be provided to a user of the delivery device by any suitable means. In one aspect, the delivery system comprises indicia correlated to the position or orientation of the valvulotome device. Any suitable form of indicia can be used to provide the user of the delivery device with information about the position and radial dimensions of the valvulotome device in a body vessel. Suitable indicia include markings on portions of the delivery device, light emitting diodes (LED) and emission of a signal from the valvulotome or delivery device.

In one aspect, markings on portions of the delivery device can correlate to the translation of a handle with the radius of the valvulotome device in a body vessel. With respect to FIG. 7A, the delivery device 700 comprises indicia 730 to correlate the translation of the proximal handle 710 with respect to the distal handle 720 to the simultaneous radial expansion of the valvulotome arms of the valvulotome device. The distal end 750 of the delivery device 700 is inserted into a body vessel. When the distal handle 720 is at a first position 732, an outer sheath 740 completely covers the valvulotome device in the radially compressed configuration. The cutting edge(s) of the valvulotome are not exposed when the distal handle 720 is in the first position 732. When the distal handle 720 is translated toward the proximal handle 710, the outer sheath 740 is gradually pulled back to radially expand the valvulotome arms of the valvulotome device in a controlled manner. At a second position 734, the valvulotome arms are partially expanded within the body vessel. At a third position 736, the outer sheath no longer covers any portion of the fully-expanded valvulotome device. The cutting edge(s) of the valvulotome are fully exposed when the distal handle 720 is in the third position 736.

In another aspect, a digital LED display or color change of an indicator region can provide information about the position or orientation of a valvulotome device in a body vessel. For example, in FIG. 7B, a proximal portion of a delivery device 760 is shown that is the same as the proximal portion of the delivery device 700 shown in FIG. 7A, except that a series of indicator lights correlate the position of the proximal handle 770 with the radial expansion of the valvulotome arms of a valvulotome device. Instead of the indicia 730 on the delivery device 700 in FIG. 7A, the proximal handle 770 has a first indicator light 772 that is illuminated when the distal handle 780 is in the first position 733, a second indicator light 774 that is illuminated when the distal handle 780 is in the second position 735, a third indicator light 776 that is illuminated when the distal handle 780 is in the third position 737.

Appropriate combinations of electronic and mechanical connections are employed in the delivery device so that the illumination of an indicator light reflects the radial deployment state of the valvulotome inside a body vessel in real time. In another aspect, the delivery system provides information via the internet as to the position, orientation or radial deployment of a valvulotome device. For example, the delivery device can transmit a signal detected by a laptop computer as, for example, an internet signal. In one aspect, the delivery system comprises one or more disposable parts.

In a fourth embodiment, the valvulotome device or delivery system can further comprise any suitable intraluminal medical device, such as a stent, an occluder, and a prosthetic venous valve. The intraluminal medical device can comprise a self expanding or balloon-expandable device. For example, one or more intraluminal medical devices can be contained within a retractable outer sheath and deployed upon retraction of the outer sheath. In one aspect, retraction of an outer sheath deploys one or more valvulotome arms and further retraction of the outer sheath deploys an implantable venous valve. Methods of supplying intraluminal medical devices are also provided, for example, for treating human or veterinary patients in which it is desirable to deploy multiple intraluminal medical devices in a body vessel, for example in conjunction with procedures using the valvulotome device.

For example, the valvulotome device or the delivery system can further comprise a prosthetic or remodelable venous valve. The delivery systems and methods can deploy different types of intraluminal medical devices in a single procedure and/or vessel. For example, it may be desirable to deploy a prosthetic venous valve at one location in a vessel, and deploy a self-expandable stent at another location in the same vessel after using a valvulotome. Thus, any suitable combination of intraluminal medical devices can be used in the devices, kits and methods described herein. Any suitable prosthetic valve can be utilized in the devices and methods. Examples of suitable valves and delivery devices are disclosed in U.S. Patents and Published Patent Application Nos. 2004/0260389A1 ("Artificial valve prosthesis with improved flow dynamics"); 2004/0186558A1 ("Implantable vascular device"); 2004/0167619A1 ("Prosthesis adapted for placement under external imaging"); 2003/0144670A1 ("Medical device delivery system"); 2003/0125795A1 ("Multiple-sided intraluminal medical device"); U.S. Pat. No. 6,508,833 ("Multiple-sided intraluminal medical device"); and U.S. Pat. No. 6,200,336 ("Multiple-sided intraluminal medical device"). Each of these references is hereby incorporated into this disclosure in its entirety for the express purpose of describing suitable implantable medical devices and delivery systems for use in and with the devices, kits, and methods described herein. The exact combination and number of intraluminal medical devices used in any particular method or included in any particular kit will depend on various factors, including the condition being treated.

In a fifth embodiment, methods of using a valvulotome device are provided herein. One method comprises the step of inserting a valvulotome device into a body vessel. For example, a delivery system can be employed to advance a valvulotome device to a first point of treatment (POT). Preferably, this step comprises advancing a delivery system that includes an outer sheath, a valvulotome device and an inner guide wire conduit through a body vessel. Alternatively, this step can comprise advancing a valvulotome device through a tube that has previously been inserted into the body vessel.

At the POT, the valvulotome device can be deployed. The manner in which this step is accomplished will depend on the arrangement of the valvulotome device within the delivery system. For example, if the valvulotome device is disposed annularly around an inner guide wire conduit, the valvulotome device can be deployed by withdrawing the outer sheath to expose the valvulotome device and allow self expansion of the valvulotome device to occur. In other embodiments, the valvulotome device can be contained within a lumen of an outer sheath previously inserted into a body vessel and pushed in its compressed configuration to a POT. At the POT, the valvulotome device can be deployed simply by forcing the medical device out of an end of a lumen.

In a sixth embodiment, methods of treatment are provided. In one aspect, a method of treating or preventing a venous valve-related condition, such as Venous Valve Insufficiency (VVI), is provided. A "venous valve related condition" means any medical condition presenting symptoms commensurate with impaired venous valve function.

Other aspects provide methods of inducing venous valve insufficiency, for example, to create an animal model with one or more insufficient venous valves.

Also provided are methods of impairing the function of one or more venous valves. More generally, methods of cutting tissue within any body vessel are provided.

In a seventh embodiment, kits comprising a valvulotome device and a delivery system are provided, including kits comprising a catheter-based delivery system and a valvulotome device. Kits comprising a valvulotome device and an implantable venous valve or stent are also provided.

FIGS. 12 through 20 illustrate a valvulotome device 1200 according to another embodiment. The valvulotome device 1200 includes outer 1210 and inner 1212 tubular members concentrically arranged about a longitudinal axis 1214. The outer tubular member 1210 has proximal 1216 and distal 1218 ends, and defines a first lumen 1220. Similarly, the inner tubular member 1212 has proximal 1222 and distal 1224 ends, and defines a second lumen 1226. The inner tubular member 1212 is disposed within the first lumen 1220. An inner member 1228 is disposed within the second lumen 1226. The inner member 1226 has proximal 1228 and distal 1230 ends, and defines an inner passageway 1232. A distal tip 1234 is disposed on the distal end 1230 of the inner member 1226.

Figure 16:
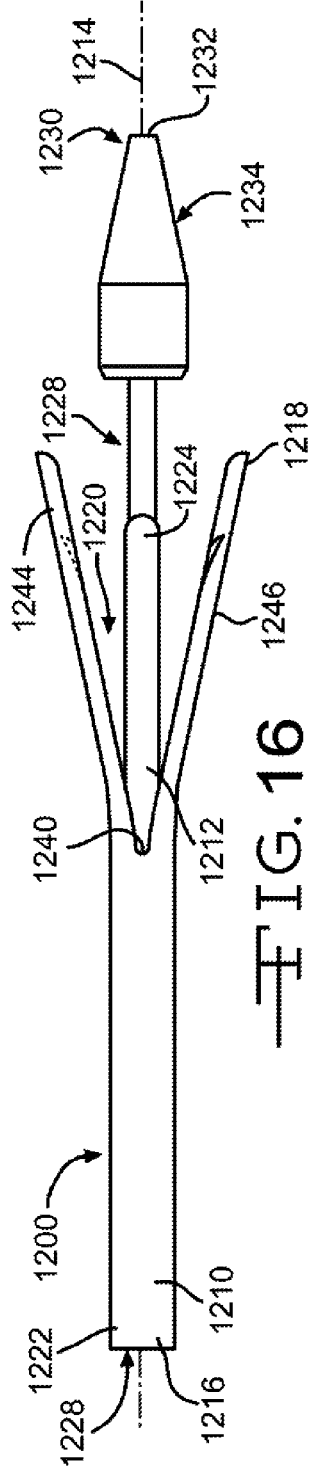
FIG. 16 is a second side view of the valvulotome device illustrate in FIG. 12.

As best illustrated in FIGS. 12 and 16, the proximal ends 1216, 1222 of the outer 1210 and inner 1212 tubular members are flush with each other. The tubular members 1210, 1212 have different axial lengths, however. In the illustrated embodiment, the distal end 1218 of the outer tubular member 1210 extends axially beyond the distal end 1224 of the inner tubular member 1212 along the longitudinal axis 1214. A reverse configuration, in which the distal end 1224 of the inner tubular member 1212 extends axially beyond the distal end 1218 of the outer tubular member 1210, could also be used. The inner tubular member is longer than both the outer 1210 and inner 1212 tubular members. Thus, as best illustrated in FIGS. 12 and 16, the distal end 1230 of the inner member 1226 extends axially beyond the distal ends 1212, 1224 of the outer 1210 and inner 1212 tubular members along the longitudinal axis 1214. Also as best illustrated in FIGS. 12 and 16, the distal tip 1234 is positioned on the longitudinal axis 1214 such that its proximal end 1232 is axially beyond the distal ends 1212, 1224 of the outer 1210 and inner 1212 tubular members with respect to the longitudinal axis 1214 and the proximal ends 1216, 1222 of the tubular member 1210, 1212.

The proximal ends 1216, 1222 of the outer 1210 and inner 1212 tubular members are advantageously attached to each other, such as with adhesives, mechanical connectors, such as crimps and other connectors, and any other suitable means for attaching. Mating threads could also be used to attach the proximal ends 1216, 1222 to each other. For example, the proximal end 1216 of the outer tubular member 1210 could define a thread on its interior surface, and the proximal end 1222 of the inner 1212 tubular member could define a mating thread on its outer surface. The proximal ends 1216, 1222 of the outer 1210 and inner 1212 tubular members could be attached to each other, in this embodiment, by simply threading the connections together. Additional means for attaching, such as an adhesive or crimp, could also be applied to the threaded connection to strengthen the attachment.

Figure 17:
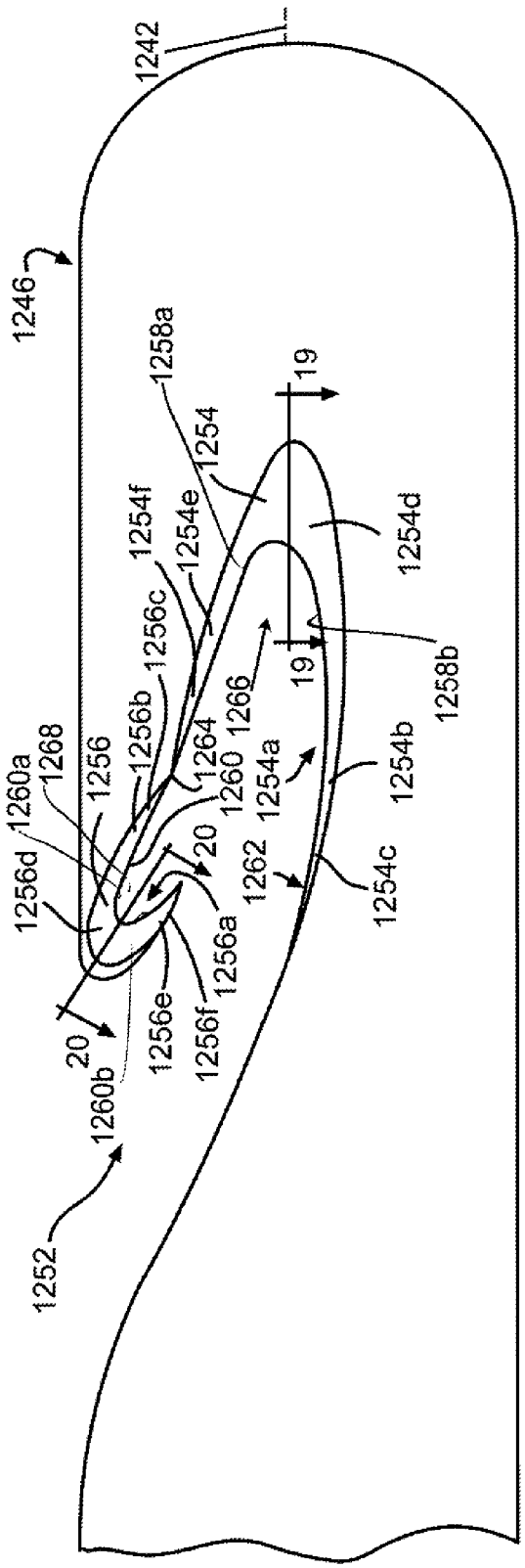
FIG. 17 is a top view of a valvulotome arm of the valvulotome device illustrated in FIGS. 12-16.

As best illustrated in FIG. 16, the outer tubular member 1210 defines first 1240 and second (not shown in the Figures) splits to form first 1244 and second 1246 valvulotome arms. Each split advantageously comprises a curve having a radius. Each of the valvulotome arms 1244, 1246 has a u-shaped curved body 1248 that forms a concave surface 1250 facing the longitudinal axis 1214 of the device 1200. The u-shaped curved body 1248 of each valvulotome arm 1244, 1246 has two oppositely facing arms that extend inward, and a base portion, comprising the bottom portion of the curved body 1248, that extends laterally between the oppositely facing arms. The concave surface 1250 defines a notch 1252 that includes first 1254 and second 1256 angled surfaces that provide first 1258 and second 1260 cutting edges that can be used to incisably engage a valve leaflet as described herein. As best illustrated in FIGS. 17 and 20, each of the angled surfaces 1254, 1256 follows a curve 1254a, 1256a along the perimeter 1262 of the notch 1252 such that the width of the angled surface 1254, 1256 tapers from a first narrow width 1254b, 1256b at a first end 1254c, 1256c of the angled surface 1254, 1256, to a relatively wide width 1254d, 1256d, and ultimately to a second narrow width 1254e, 1256e at a second end 1254f, 1256f of the angled surface 1254, 1256. The wide width 1254d, 1256d is positioned between the first 1254b, 1256b and second 1254e, 1256e narrow widths. The second ends 1254f, 1256f of the angled surfaces 1254, 1256 terminate at a point 1264 inside the perimeter of the notch 1252. The inclusion of the first 1254 and second 1256 angled surfaces, and first 1258 and second 1260 cutting edges, is considered advantageous at least because they provide multiple contact points at which the valvulotome arms 1244, 1246 can incisably engage a valve leaflet in vivo. Furthermore, the curved structure and varying widths of the first 1254 and second 1256 angled surfaces is expected to increase the efficiency of leaflet engagements by forming two substantially opposing cutting arcs 1266, 1268. Furthermore, the relative positioning of the first 1254 and second 1256 angled surfaces, and their co-termination at point 1264, is expected to aid leaflet incision by drawing an engaged leaflet into one of the cutting arcs 1266, 1268 where each cutting edge 1258, 1260 includes opposing portions 1258a, 1258b, 1260a, 1260b.

It is noted that, while the Figures illustrate this embodiment with first 1266 and second 1268 cutting arcs, the second cutting arc 1268, or outermost cutting arc, is considered optional and can be eliminated from one or both of the valvulotome arms 1244, 1246. In this alternative embodiment, the first 1254 and second 1256 angled surfaces that provide first 1258 and second 1260 cutting edges could still be present and could still co-terminate at point 1264. The second cutting edge 1260 would simply extend along a substantially straight line to the lateral side of the appropriate valvulotome arm. Alternatively, the second angled surface 1256 and second cutting edge 1260 could also be eliminated.

In contrast to the embodiments described above, such as the embodiments illustrated in FIGS. 3, 4, 5, and 6, the notch 1252 of each valvulotome arm 1244, 1246 of this embodiment is positioned such that the notch 1252 extends into the base of the u-shaped curved body 1248. The notches of the embodiments described above are positioned on the arms of the u-shaped curved body, and do not extend into the base of the u-shaped curved body 1248. Each of the valvulotome arms of the embodiment illustrated in FIG. 4, for example, includes a notch in each arm of the u-shaped curved body, which allows each valvulotome arm to have two notches. As best illustrated in FIG. 14, the notch 1252 of each valvulotome arm 1244, 1246 of this embodiment has an open end on one of the arms of the u-shaped curved body 1248 and extends into the base of the u-shaped curved body 1248 such that the first cutting arc 1266 is positioned near, at, or on the midpoint of the lateral width of the u-shaped curved body 1248. The inventors have determined that this positioning of the notch 1252 provides an advantageous positioning of the angled surfaces 1254, 1256 that is expected to increase the efficiency with which the valvulotome incisably engages valve leaflets in vivo.

It is noted that, while each valvulotome arm 1244, 1246 of the illustrated embodiment includes a notch, a suitable valvulotome device can have any suitable number of valvulotome arms and any suitable number of notches, including a number of notches that is less than the number of valvulotome arms. All that is required is that at least one of the valvulotome arms in any given embodiment define a notch. The inventors have determined, though, that a valvulotome device, such as the illustrated device 1200, in which each valvulotome arm forms a notch, and its associated angled surface and cutting edge, is particularly advantageous.

The structural arrangement of the notch 1252 on the u-shaped curved body 1248 illustrated for this embodiment is considered particularly advantageous. As best illustrated in FIG. 17, the notch 1252 is advantageously positioned on the u-shaped curved body 1248 such that the apex 1254g of the curve 1254a of the first angled surface 1254 is positioned substantially adjacent or on a longitudinal axis 1242 of the corresponding valvulotome arm 1244, 1246. The inventors believe that this structural arrangement of the notch 1252 on the u-shaped curved body 1248 will better position the angled surface 1254 and its cutting edge 1258 relative to a valve leaflet attached to a wall of a vessel within which the valvulotome device 1200 is being used.

As best illustrated in FIG. 12, the inner tubular member 1212 defines third 1270 and fourth (not shown in the Figures) splits to form first 1274 and second 1276 spacing arms. Each split advantageously comprises a curve having a radius. Similar to the valvulotome arms 1244, 1246, each of the spacing arms 1274, 1276 has a u-shaped curved body 1278 that forms a concave surface 1280 facing the longitudinal axis 1214 of the device 1200. In contrast to the valvulotome arms 1244, 1246, however, the spacing arms do not include a notch, angled surface, or cutting edge.

As best illustrated in FIG. 13, the outer tubular member 1210 has an outer diameter that is greater than the outer diameter of the inner tubular member 1212. As a result, the spacing arms 1274, 1276 formed by the inner tubular member 1212 can be concentrically wrapped by the valvulotome arms 1244, 1246 formed by the outer tubular member 1210 when the valvulotome device 1200 is in a radially compressed configuration (i.e., when all arms 1244, 1246, 1274, 1276 are collapsed inward on the inner member 1228, such as when the device 1200 is stored within a delivery system for navigation through a body vessel). This concentric arrangement of the tubular members 1210, 1212 contributes to the overall compact design of the valvulotome device 1200.

The inner passageway 1232 of the inner member 1226 provides a lumen through which a wireguide or other placement device can be passed, facilitating navigation of the valvulotome device 1200 to a point of treatment in a body vessel. The distal tip 1234 on the distal end 1230 of the inner member 1226 is advantageously an atraumatic tip, including a tapered distal surface 1282 and a tapered proximal surface 1284. As best illustrated in FIGS. 12 and 16, the proximal end 1228 of the inner member 1226 is advantageously flush with the proximal ends 1216, 1222 of the outer 1210 and inner 1212 tubular members. In this configuration, the valvulotome 1200 provides a structural unit that can easily be attached to a blunt end member to form a delivery device (described in further detail below). It is noted, though, that the inner member 1226 can alternatively extend axially beyond the proximal ends 1216, 1222 of one or both outer 1210 and inner 1212 tubular members in the proximal direction (to the left side of FIGS. 12 and 16).

The outer 1210 and inner 1212 tubular can be formed from any suitable material. Skilled artisans will be able to select a suitable material based on various considerations, including biocompatibility, desired strength, and workability. Examples of suitable types of materials include metals, plastics, other polymeric materials, and ceramics. Metals are considered particularly advantageous at least because of their ability to be formed with suitable cutting edges. Shape memory metals are considered particularly advantageous. Nickel titanium alloys are considered particularly advantageous. Cold drawn cobalt chromium alloys, such as ASTM F562 and ASTM F1058 (commercial examples of which include MP35N™ and Elgiloy™, both of which are available from Fort Wayne Metals, Fort Wayne, Ind.; MP35N is a registered trademark of SPS Technologies, Inc. (Jenkintown, Pa., USA); Elgiloy is a registered trademark of Combined Metals of Chicago LLC (Elk Grove Village, Ill., USA)), are currently considered advantageous materials at least because they are non-magnetic materials that provide beneficial magnetic resonance imaging (MRI) compatibility, and avoid MRI artifacts typically associated with some other materials, such as stainless steel. Nickel-cobalt-chromium-molybdenum alloys, such as MP35N, are also considered particularly advantageous at least because of the relatively high tensile strength provided by these materials.

Figure 21:
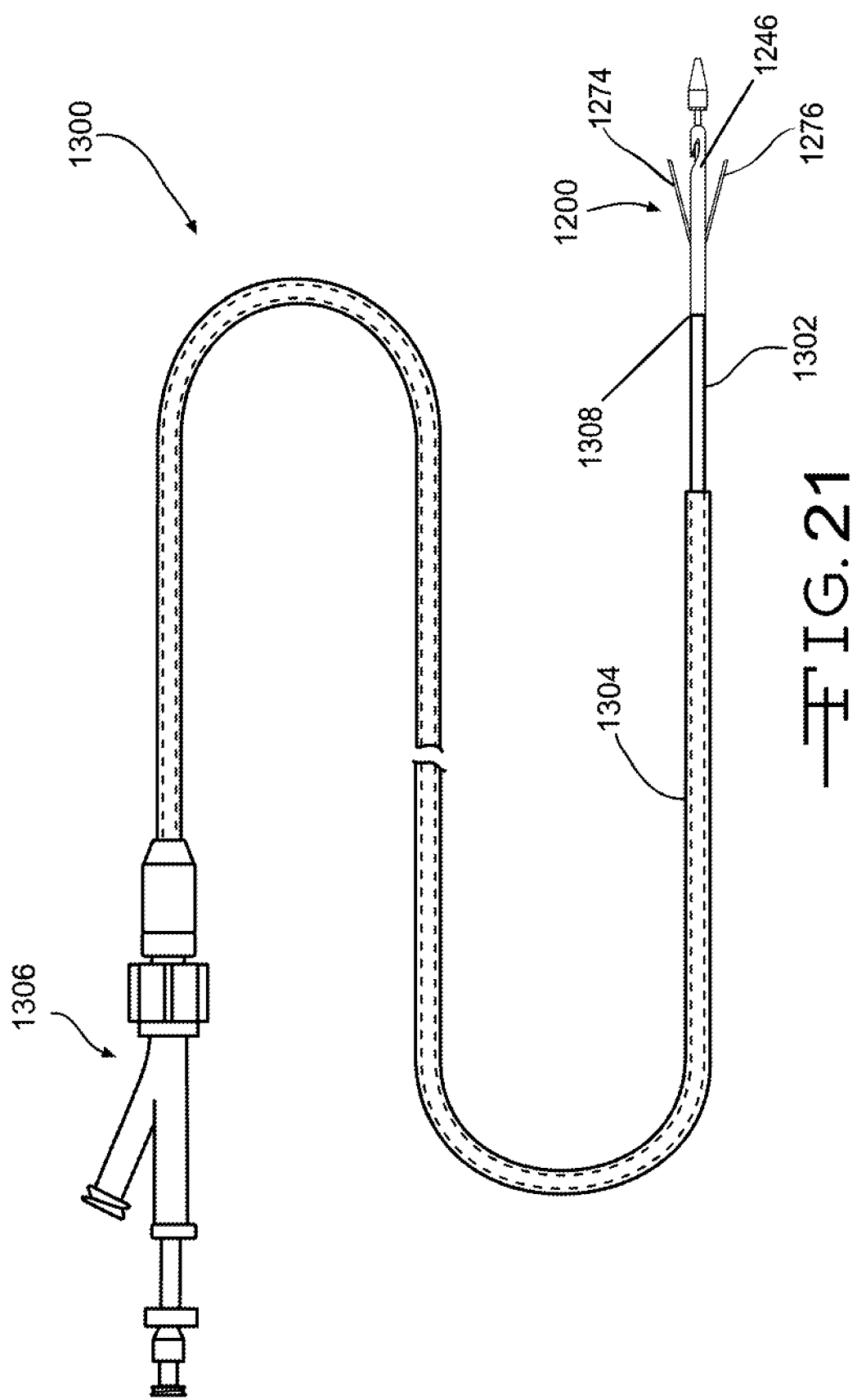
FIG. 21 is a perspective view of a delivery system.

FIG. 21 illustrates a delivery device 1300 comprising the valvulotome device 1200 illustrated in FIGS. 12 through 20 and described above. The proximal end of the valvulotome device 1200 is joined to the distal end of an elongate inner member 1302 that is slideably disposed within the lumen of an elongate sheath 1304. A handle 1306 is operably connected to the elongate sheath 1304 and can include various connectors, ports, and the like.

The valvulotome device 1200 is easily incorporated into the delivery device 1300 by attaching the proximal end of the device 1200 to the distal end of the elongate inner member 1302. As illustrated in the figure, a simple butt joint is considered suitable for this attachment, and can be formed using adhesives, mechanical connectors, such as staples, crimps, and other connectors, and any other suitable mechanical means for attaching. Mating threads could also be used to attach the proximal end of the device 1200 to the distal end of the elongate inner member 1302.

Alternatively, the valvulotome device can be formed such that it provides the elongate inner member. For example, one or more of the outer tubular member, inner tubular member, and inner member can extend the full length of the delivery device 1300. In these embodiments, one or more of the outer tubular member, inner tubular member, and inner member can include structural features that provide additional flexibility to the element. For example, the outer tubular member can include a spiral cut along a portion of, a substantial portion of, the majority of, or the entire length from the proximal end to the split forming the valvulotome arms.

A user operates the delivery system by advancing and/or retracting one or both of the elongate inner member 1302 and elongate sheath 1304 relative to each other to effect expansion of the valvulotome arms 1244, 1246 and spacing arms 1274, 1276 from a radially compressed configuration to the radially expanded configuration illustrated in FIG. 21. Once the arms are expanded in a body vessel, the user manipulates the elongate inner member 1302 to position one or both of the valvulotome arms 1244, 1246 adjacent a valve leaflet in the body vessel to incisably engage the leaflet.

Figure 22:
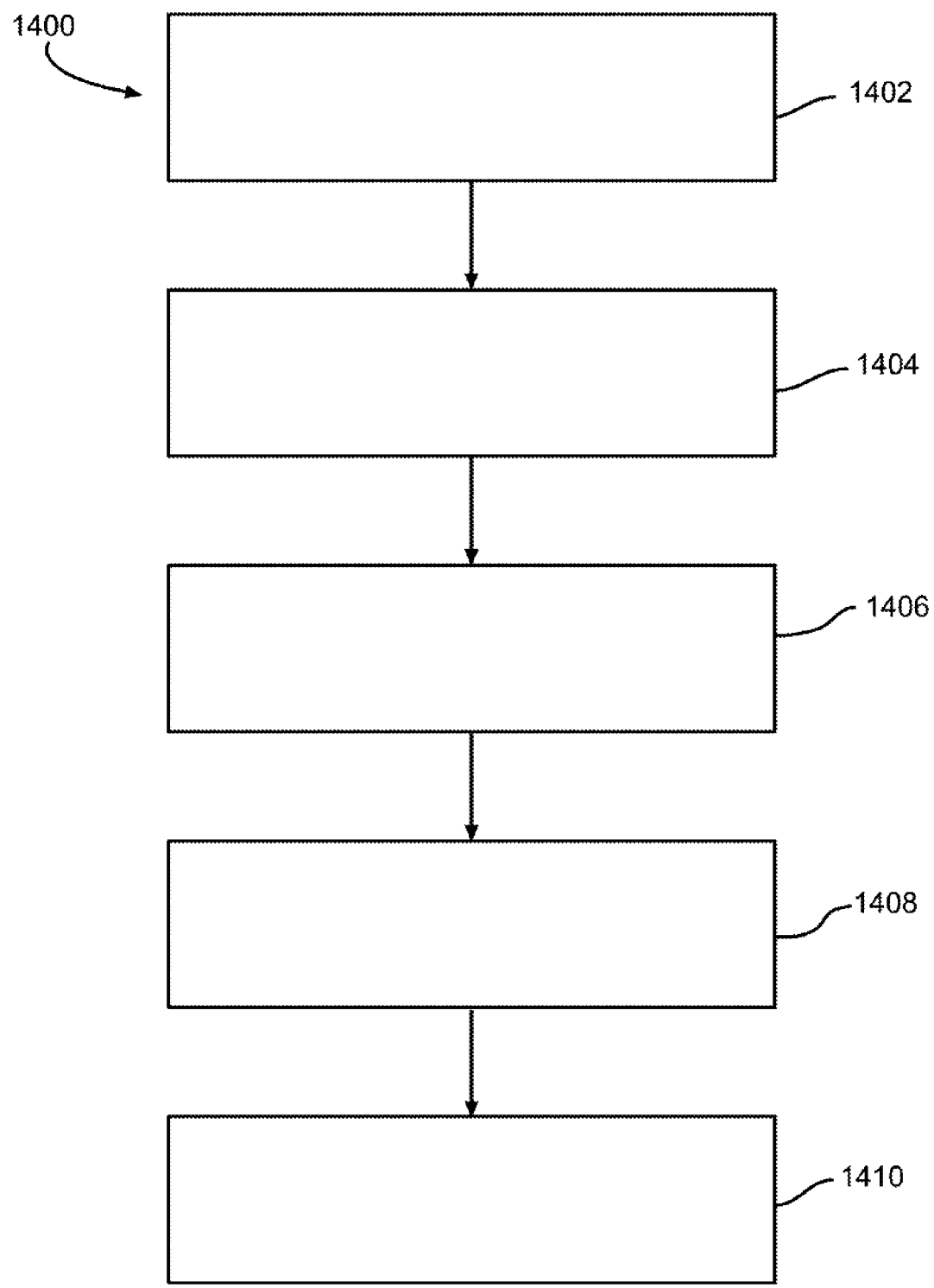
FIG. 22 is a flowchart illustrating a method of making a valvulotome device.

FIG. 22 is a flowchart representing an exemplary method of making 1400 valvulotome device. A first step 1402 comprises providing first and second tubular members, such as the first and second tubular members described above, and an inner member, such as the inner member described above. A second step 1404 comprises cutting the first tubular member to form first and second valvulotome arms, such as the valvulotome arms described above. A third step 1406 comprises cutting the second tubular member to create a second split that firms first and second spacing arms. A fourth step 1408 comprises placing the second tubular member in the lumen defined by the first tubular member. A fifth step 1410 comprises placing the inner member in the lumen defined by the first tubular member.

The first step 1402 advantageously comprise providing first and second tubular members formed of a biocompatible metal, such as stainless steel or a shape memory alloy. The first step 1402 particularly advantageously comprises providing first and second tubular members formed of a nickel titanium alloy. The second 1404 and third 1406 steps are advantageously conducted by laser cutting the first and second tubular members to form splits forming an inner curve and the desired arms, such as the splits described above. The second 1404 step advantageously comprises cutting the first tubular member such that each of the valvulotome arms comprises a u-shaped curved body having two oppositely facing arms that extend inward, and a base portion, comprising the bottom portion of the u-shaped curved body, that extends laterally between the oppositely facing arms. The second step 1404 particularly advantageously includes cutting the first tubular member such that each of the valvulotome arms includes a notch that opens to one of the arms of the u-shaped curved body and includes an angled surface and a cutting edge positioned on the base portion of the u-shaped curved body.

Optional steps, which can be included individually or in any combination, include orienting the proximal ends of the first and second tubular members so that they are flush with each other; orienting the proximal end of the inner member so that it is flush with the proximal end of one or both of the first and second tubular members; attaching the first and second tubular members to each other, such as with an adhesive; attaching the inner member to one or both of the first and second tubular members; and circumferentially orienting the first tubular member such that the valvulotome arms are circumferentially spaced from the spacing arms by a desired angle, such as approximately 90°.

The foregoing disclosure includes the best mode known to the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

The recitations of "embodiments," "one embodiment," "some embodiments," "other embodiments," "illustrative embodiments," "selected embodiments," "certain embodiments," and "another embodiment" herein are synonymous. All of these recitations, and "aspects" thereof, refer to illustrative embodiments and are not exclusive of each other or of other embodiments not recited herein. Accordingly, the invention also provides embodiments that comprise combinations of one or more of the illustrative embodiments described above.

All references cited herein are hereby incorporated into this disclosure in their entirety.

EXAMPLES

The following Examples are offered for the purpose of illustrating the present invention and are not to be construed to limit the scope of this invention. Any combination of features described in embodiments of the invention, including those provided below, are also within the scope of the invention.

Example 1

A Four-Staggered Valvulotome Arm Valvulotome Device Having Four Cutting Edges

Figure 8A:
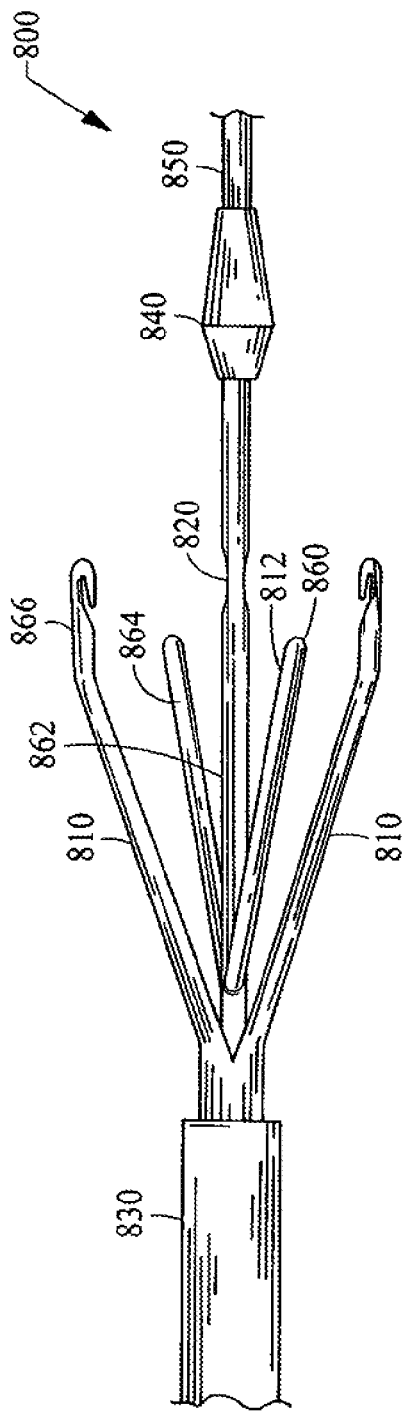
Figure 8B:
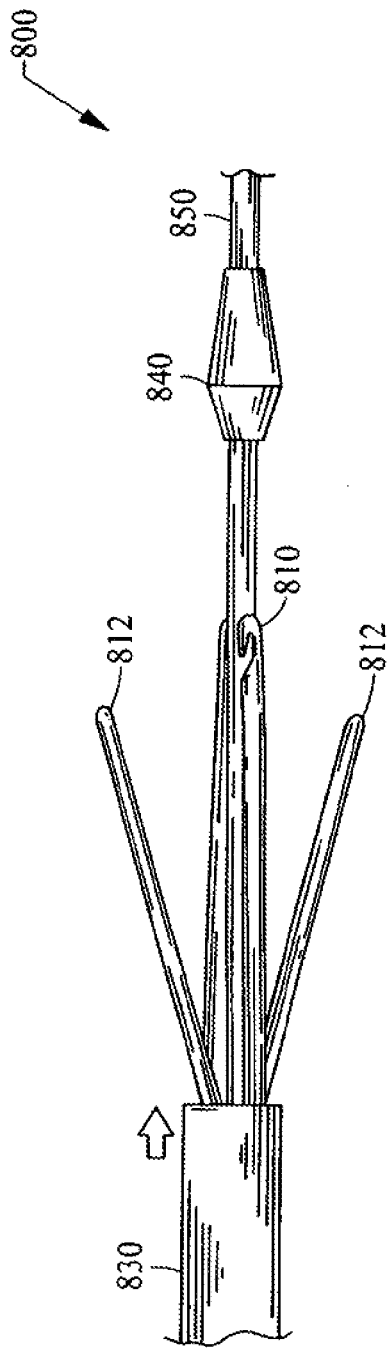

FIG. 8A and FIG. 8B show a portion of a first valvulotome device 800 comprising two longer valvulotome arms 810 radially disposed in an alternating fashion with two shorter valvulotome arms 812. The longer valvulotome arms 810 are formed from laser-cut NiTi alloy and have a curved cross section with an outside diameter of 0.086-inch. The short valvulotome arms 812 are formed from laser-cut NiTi alloy and have a curved cross section with an outside diameter of 0.065-inch. Each of the longer valvulotome arms 810 and the shorter valvulotome arms 812 comprise a probe 860, a guiding edge 862 and a cutting edge 864 to form a notch at the distal end of each valvulotome arm. The longer valvulotome arm 810 has a greater length than the shorter valvulotome arms 812, and the distal ends of the longer valvulotome arm 810 have a curved portion 866 that align the cutting edge 864 to be substantially parallel to a guidewire 850. The shorter valvulotome arms 812 are straight, without a curved portion. In this example, each valvulotome arm is positioned at a 90.degree. angle with respect to every other valvulotome arm. FIG. 8C and FIG. 8D show a compressed configuration, where the shorter valvulotome arms 812 are staggered with the longer valvulotome arms 810 so as to promote closing of the device to a compressed configuration. Translation of either an outer sheath 830 toward the radiopaque tip 840, or translation of the valvulotome arms away from the radiopaque tip 840, compresses the arms into the compressed configuration. The valvulotome arms shown are laser-cut from a NITINOL® cannula.

The portion of the first valvulotome device 800 shown in FIG. 8A also includes an outer sheath 830 containing the cutting valvulotome arms 810 and the guiding valvulotome arms 812, an inner guide wire conduit 820, a guidewire 850 and a radiopaque tip 840. The valvulotome arms are pressed against the inner guide wire conduit 820 in the compressed configuration. The radiopaque tip 840 is made of stainless steel and is readily visible in a body vessel using imaging techniques such as x-rays. The first valvulotome device 800 can be translated along the guidewire 850 to a point of treatment.

Example 2

A Four-Valvulotome-Arm Valvulotome Device Having Four Cutting Edges

Figure 9C:
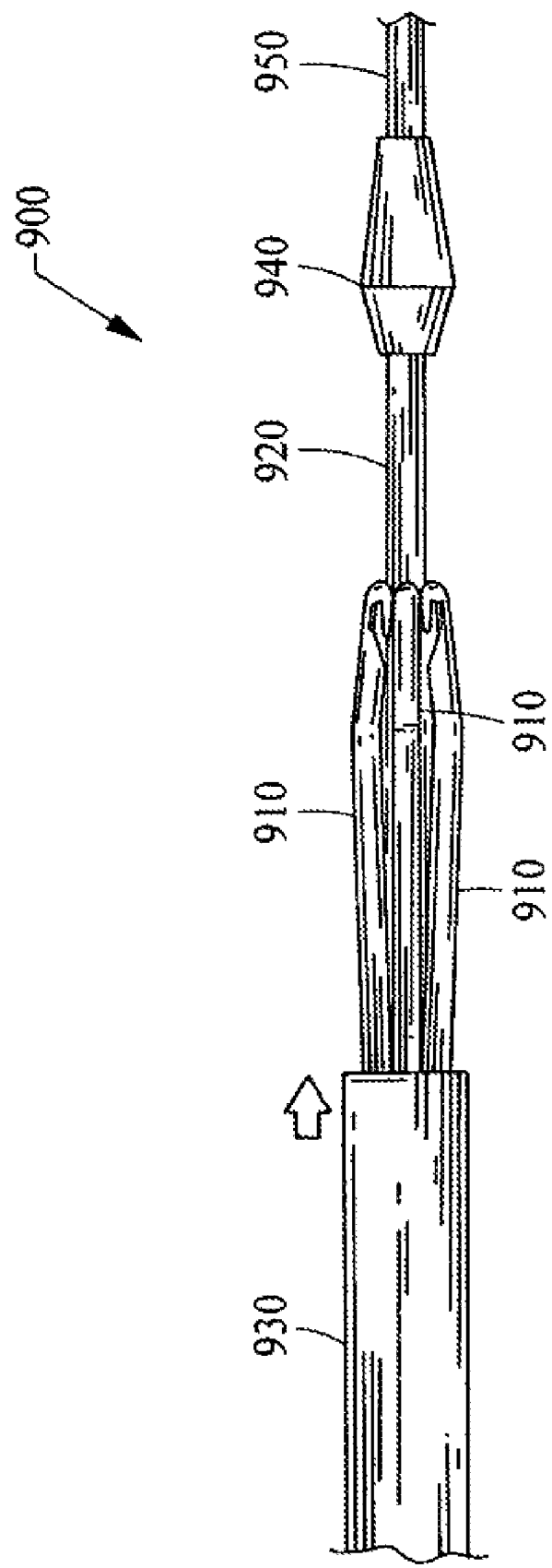

FIG. 9A, FIG. 9B, and FIG. 9C show a portion of a second exemplary valvulotome device 900 comprising four valvulotome arms of equal length. Each valvulotome arm 910 has a probe 960, a guiding edge 962 and a cutting edge 964. This valvulotome device 900 is similar to the first valvulotome device 800, except that each valvulotome arm is the same length. As seen in FIG. 9B, the second valvulotome device 900 also comprises an outer sheath 930, an inner guide wire conduit 920, a radiopaque tip 940 and a guidewire 950. As seen in FIG. 9C, the radiopaque tip 940 is positioned closer to the distal end of the valvulotome arms 910 in the compressed state, as compared to the first valvulotome device 800.

Example 3

A Two-Valvulotome-Arm Valvulotome Device Having Two Cutting Edges

FIG. 10A shows a portion of a third exemplary valvulotome device 1000 having two valvulotome arms 1010 oppositely disposed from each other, as well as an inner guide wire conduit 1020 and a radiopaque tip 1040. As seen in FIG. 10B and FIG. 10C, each valvulotome arm 1010 comprises a guiding edge 1062, a cutting edge 1064 and a probe 1060 that together define a notch. In this example, each valvulotome arm is positioned at 180.degree. from the other. The third valvulotome device 1000 is otherwise similar to the first valvulotome device 800.

Example 4

Figure 11A:
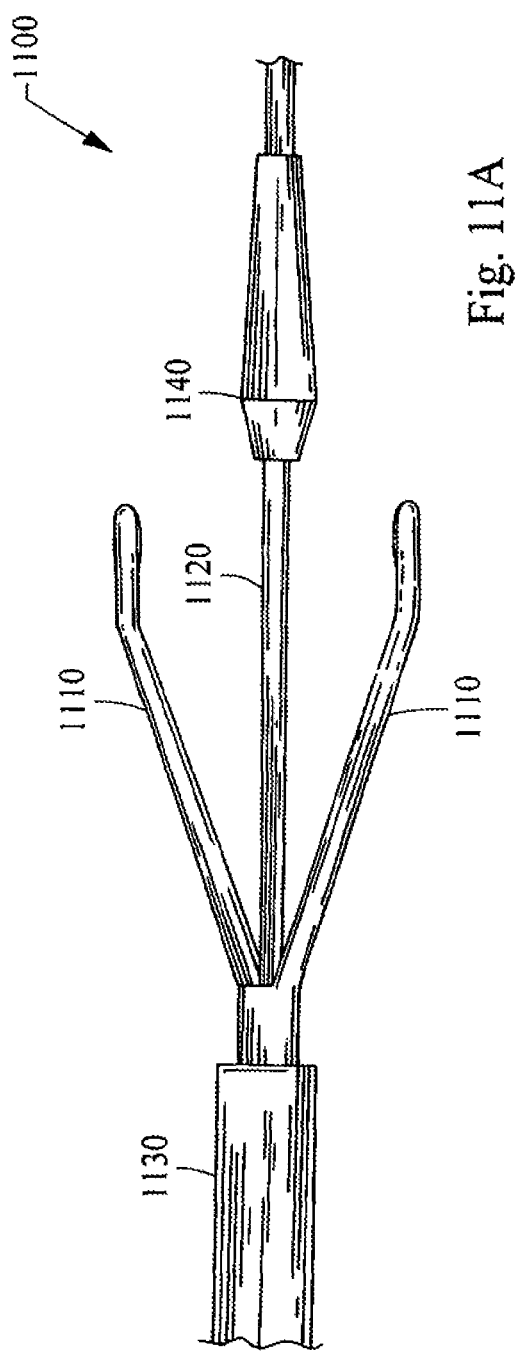
FIG. 11A, FIG. 11B, FIG. 11C and FIG. 11D depict a ninth valvulotome device.
Figure 11B:
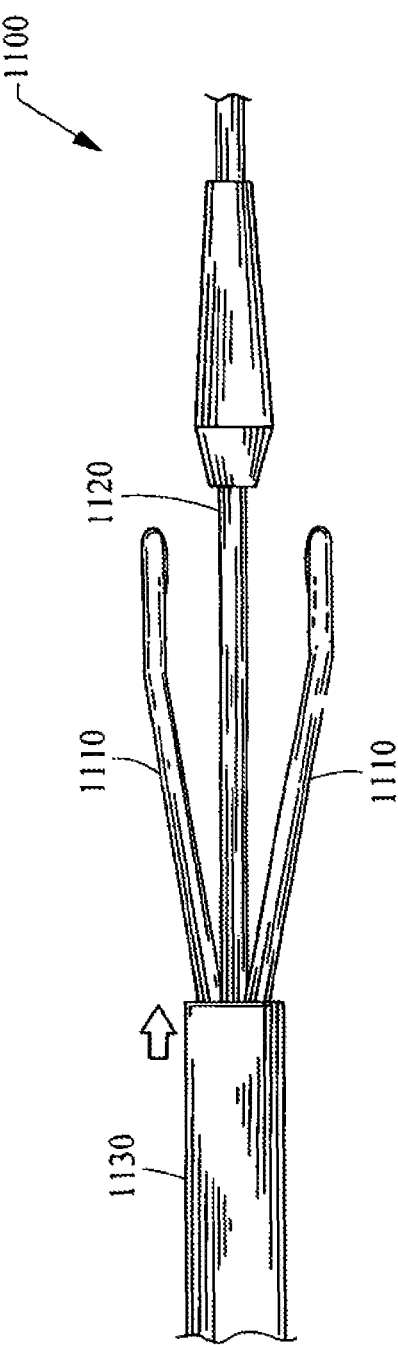
Figure 11C:
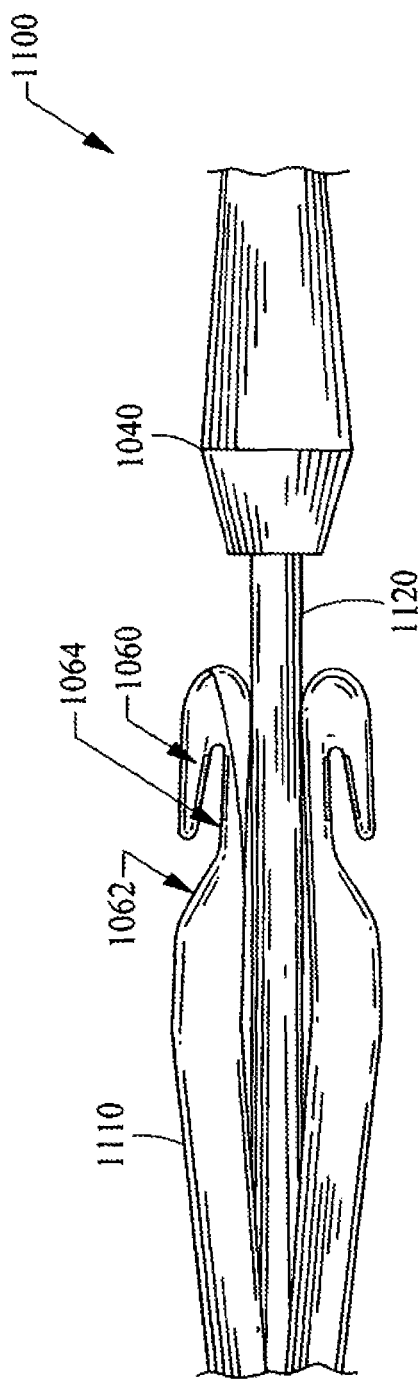
Figure 11D:
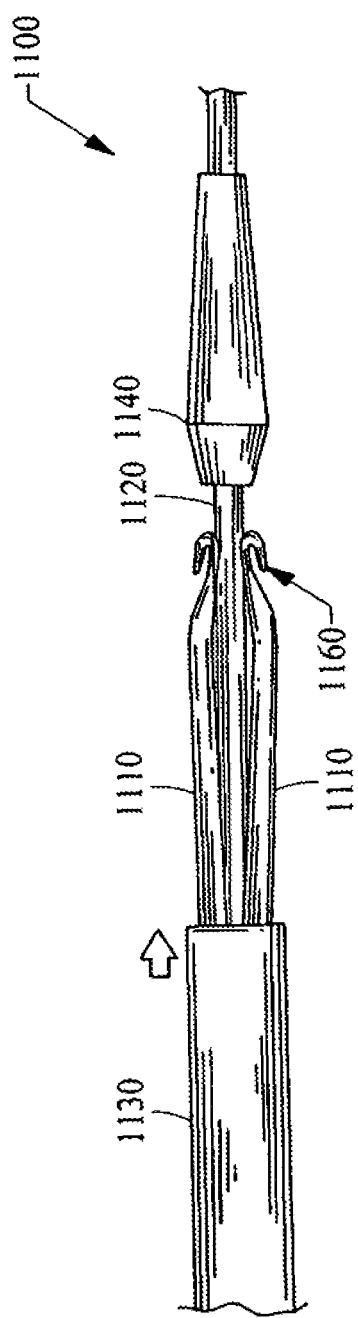

A Two-Valvulotome-Arm Valvulotome Device Having Tapered Valvulotome Arms and an Inward-Facing Probe FIG. 11A and FIG. 11B show a portion of a fourth exemplary valvulotome device 1100 having two valvulotome arms 1110 oppositely disposed around an inner guide wire conduit 1120. As shown in FIG. 11C and FIG. 11D, each valvulotome arm 1110 has a probe 1160, a guiding edge 1162 and a cutting edge 1164. The radiopaque tip 1140 is more elongated than that of the first valvulotome device 800. Translation of the outer sheath 1130 toward the radiopaque tip 1140 compressed the valvulotome arms against the inner guide wire conduit 1120 from the expanded configuration to the compressed configuration. In this example, each valvulotome arm is positioned at 180.degree. with respect to the other valvulotome arm. The fourth valvulotome device 1100 is otherwise similar to the first valvulotome device 800.

We claim:

1. A valvulotome device, comprising:
a tubular member having a proximal end, a distal end, a lengthwise axis, and defining a first lumen, the tubular member forming first and second valvulotome arms having a radially compressed and radially expanded configurations, each of the first and second valvulotome arms having a u-shaped curved body comprising opposing first and second arms and a base portion extending between the first and second arms, at least one of the first and second valvulotome arms defining a notch having an open end on one of the first and second arms of the u-shaped curved body and extending into the base portion of the u-shaped curved body, the notch defining an angled surface that provides a cutting edge.

2. The valvulotome device of claim 1, wherein the first valvulotome arm defines a first notch having an open end on one of the first and second arms of the u-shaped curved body of the first valvulotome arm and extending into the base portion of the u-shaped curved body of the first valvulotome arm, the first notch defining a first angled surface that provides a first cutting edge; and
wherein the second valvulotome arm defines a second notch having an open end on one of the first and second arms of the u-shaped curved body of the second valvulotome arm and extending into the base portion of the u-shaped curved body of the second valvulotome arm, the second notch defining a second angled surface that provides a second cutting edge.

3. The valvulotome device of claim 1, wherein the cutting edge has first and second opposing portions to form a cutting arc.

4. The valvulotome device of claim 1, wherein the at least one of the first and second valvulotome arms that defines the notch has a valvulotome arm longitudinal axis and the u-shaped curved body has a lateral width having a midpoint; and
wherein the cutting arc traverses the midpoint of the lateral width of the u-shaped curved body.

5. The valvulotome device of claim 4, wherein the cutting arc has an apex positioned substantially adjacent the valvulotome arm longitudinal axis.

6. The valvulotome device of claim 4, wherein the cutting arc has an apex positioned on the valvulotome arm longitudinal axis.

7. The valvulotome device of claim 1, wherein the tubular member comprises first and second splits that cooperatively form the first and second valvulotome arms.

8. The valvulotome device of claim 7, wherein each of the first and second splits comprise a curve having a radius.

9. The valvulotome device of claim 7, wherein the first split is positioned substantially opposite the second split with respect to the lengthwise axis of the tubular member.

10. The valvulotome device of claim 1, wherein the tubular member comprises a material selected from the group consisting of metals, polymerics, and ceramics.

11. The valvulotome device of claim 1, wherein the tubular member comprises stainless steel.

12. The valvulotome device of claim 1, wherein the tubular member comprises a shape memory metal.

13. The valvulotome device of claim 12, wherein the shape memory metal comprises nickel titanium.

14. A valvulotome device, comprising:
an outer tubular member having a first proximal end, a first distal end, a first lengthwise axis, and defining a first lumen, the outer tubular member forming first and second valvulotome arms having radially compressed and radially expanded configurations, each of the first and second valvulotome arms having a u-shaped curved body comprising opposing first and second arms and a base portion extending between the first and second arms, at least one of the first and second valvulotome arms defining a notch having an open end on one of the first and second arms of the u-shaped curved body and extending into the base portion of the u-shaped curved body, the notch defining an angled surface that provides a cutting edge; and
an inner tubular member having a second proximal end, a second distal end, a second lengthwise axis, and defining a second lumen, the inner tubular disposed in the first lumen defined by the outer tubular member and forming first and second spacing arms having radially compressed and radially expanded configurations.

15. The valvulotome device of claim 14, wherein the first proximal end is positioned flush with the second proximal end.

16. The valvulotome device of claim 14, wherein the outer tubular member is circumferentially oriented about the first longitudinal axis such that each of the first and second valvulotome arms is circumferentially spaced from each of the first and second spacing arms by an angle of approximately 90°.

17. The valvulotome device of claim 14, wherein at least one of the outer tubular member and the inner tubular member comprises stainless steel.

18. The valvulotome device of claim 14, wherein at least one of the outer tubular member and the inner tubular member comprises a shape memory metal.

19. The valvulotome device of claim 14, wherein the shape memory metal comprises nickel titanium.

20. A valvulotome device, comprising:
- an outer tubular member having a first proximal end, a first distal end, a first lengthwise axis, and defining a first lumen, the outer tubular member forming first and second valvulotome arms having radially compressed and radially expanded configurations, each of the first and second valvulotome arms having a u-shaped curved body comprising opposing first and second arms and a base portion extending between the first and second arms, the first valvulotome arm defining a first notch having an open end on one of the first and second arms of the u-shaped curved body of the first valvulotome arm and extending into the base portion of the u-shaped curved body of the first valvulotome arm, the first notch defining a first angled surface that provides a first cutting edge, the second valvulotome arm defining a second notch having an open end on one of the first and second arms of the u-shaped curved body of the second valvulotome arm and extending into the base portion of the u-shaped curved body of the second valvulotome arm, the second notch defining a second angled surface that provides a second cutting edge; and
- an inner tubular member having a second proximal end, a second distal end, a second lengthwise axis, and defining a second lumen, the inner tubular disposed in the first lumen defined by the outer tubular member and forming first and second spacing arms having radially compressed and radially expanded configurations;
- wherein the first proximal end is positioned flush with the second proximal end; and
- wherein the outer tubular member is circumferentially oriented about the first longitudinal axis such that each of the first and second valvulotome arms is circumferentially spaced from each of the first and second spacing arms by an angle of approximately 90°.

* * * * *